US012315621B2

(12) United States Patent
Sengupta et al.

(10) Patent No.: US 12,315,621 B2
(45) Date of Patent: May 27, 2025

(54) CARDIAC ULTRASONIC FINGERPRINTING: AN APPROACH FOR HIGHTHROUGHPUT MYOCARDIAL FEATURE PHENOTYPING

(71) Applicant: RUTGERS, THE STATE UNIVERSITY OF NEW JERSEY, New Brunswick, NJ (US)

(72) Inventors: Partho P. Sengupta, Morgantown, WV (US); Sirish Shrestha, Morgantown, WV (US); Nobuyuki Kagiyama, Morgantown, WV (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 723 days.

(21) Appl. No.: 17/617,465

(22) PCT Filed: Jun. 11, 2020

(86) PCT No.: PCT/US2020/037204
§ 371 (c)(1),
(2) Date: Dec. 8, 2021

(87) PCT Pub. No.: WO2020/257046
PCT Pub. Date: Dec. 24, 2020

(65) Prior Publication Data
US 2022/0238208 A1 Jul. 28, 2022

Related U.S. Application Data

(60) Provisional application No. 62/864,771, filed on Jun. 21, 2019.

(51) Int. Cl.
*G16H 30/40* (2018.01)
*A61B 8/00* (2006.01)
(Continued)

(52) U.S. Cl.
CPC .......... *G16H 30/40* (2018.01); *A61B 8/0883* (2013.01); *A61B 8/5223* (2013.01);
(Continued)

(58) Field of Classification Search
None
See application file for complete search history.

(56) References Cited

U.S. PATENT DOCUMENTS

2008/0025592 A1* 1/2008 Jerebko ................ G06T 11/005
382/132
2009/0016586 A1 1/2009 Gardner et al.
(Continued)

OTHER PUBLICATIONS

PCT International Search Report in co-pending, related PCT Application No. PCT/US2020/037204, mailed Sep. 2, 2020.
(Continued)

*Primary Examiner* — Wen W Huang
(74) *Attorney, Agent, or Firm* — Quarles & Brady LLP

(57) ABSTRACT

Disclosed are systems and methods associated with myocardial ultrasonic fingerprinting using a radiomics-based approach and high-throughput computing on static cardiac ultrasound images. Radiomic features can be extracted from an ultrasound image associated with a patient. Myocardial characteristics are then determined by using the extracted features as inputs into trained phenotyping models. A clinical significance associated with the patient can then be interpreted based at least in part on the myocardial characteristics and the extracted radiomic features.

18 Claims, 16 Drawing Sheets

(51) Int. Cl.
  *A61B 8/08* (2006.01)
  *G06T 7/00* (2017.01)
  *G16H 30/20* (2018.01)
  *G16H 50/20* (2018.01)
  *G16H 50/30* (2018.01)

(52) U.S. Cl.
  CPC ........... *G06T 7/0012* (2013.01); *G16H 30/20* (2018.01); *G16H 50/20* (2018.01); *G16H 50/30* (2018.01)

(56) References Cited

U.S. PATENT DOCUMENTS

| | | | |
|---|---|---|---|
| 2011/0082371 A1* | 4/2011 | Chono | A61B 6/5235 600/443 |
| 2014/0107936 A1 | 4/2014 | Janevski et al. | |
| 2014/0200240 A1 | 7/2014 | Gabriel | |
| 2015/0112182 A1* | 4/2015 | Sharma | A61B 5/0261 600/408 |
| 2016/0022375 A1* | 1/2016 | Blake | G16H 50/00 600/424 |
| 2016/0166209 A1* | 6/2016 | Itu | A61B 6/5217 600/408 |
| 2019/0362855 A1* | 11/2019 | Ma | G06T 7/0016 |

OTHER PUBLICATIONS

Retson et at. "Machine Learning and Deep Neural Networks in Thoracic and Cardiovascular Imaging", UC San Diego Previously Published Works, May 1, 2019. Retrieved on Aug. 14, 2020. Retrieved from <URL: https://escholarship.org/contentlqt6kb012qf/qt6kb012qf.pdf> entire document.

Bakas et al. "Data Descriptor: Advancing The Cancer Genome Atlas glioma MRI collections with expert segmentation abels and radiomic features", Scientific Data, Sep. 5, 2017. Retrieved on Aug. 14, 2020. Retrieved on <URL: https://www.nature.com/articles/sdata2017117 .pdf> entire document.

* cited by examiner

409

Normal myocardium

503a

Myocardial Infarction

503b

Patients with High-risk Myocardium

GLS=-8.6%, LVEF=42%   GLS=-5.0%, LVEF=14%   GLS=-8.4%, LVEF=25%

Patients with Low-risk Myocardium

GLS=-20%, LVEF=60%   GLS=-28%, LVEF=70%   GLS=-24%, LVEF=71%

CARDIAC ULTRASONIC FINGERPRINTING: AN APPROACH FOR HIGHTHROUGHPUT MYOCARDIAL FEATURE PHENOTYPING

CROSS-REFERENCE TO RELATED APPLICATIONS

This application is a national stage entry pursuant to 35 U.S.C. § 371 of Patent Cooperation Treaty (PCT) international application No. PCT/US2020/037204, filed on Jun. 11, 2020, which claims priority to, and the benefit of, co-pending U.S. provisional application entitled "CARDIAC ULTRASONIC FINGERPRINTING: AN APPROACH FOR HIGH-THROUGHPUT MYOCARDIAL FEATURE PHENOTYPING" having Ser. No. 62/864,771, filed on Jun. 21, 2019, which are all hereby hereby incorporated by reference in their entireties.

BACKGROUND

Tissue characterization of myocardial pathology has been one of the greatest interests in the field of cardiac imaging. Advancement in noninvasive imaging techniques, especially cardiac magnetic resonance and echocardiography, has revealed that myocardial imaging features can be tightly associated with the pathological findings and provide valuable risk stratification. To that end, although cardiac ultrasound is considered the most accessible first-line imaging diagnostic tool that can accurately assess myocardial function and flow dynamics, ultrasound images endure significant impediments with regards to accurate tissue characterization. Although various attempts have been made to improve tissue characterization using B-mode image videodensitometry techniques and integrated backscatter, the limitations in tissue characterization using cardiac ultrasound have predominantly been due to variant intensities and image quality from echocardiography.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

SUMMARY

Figure 1:
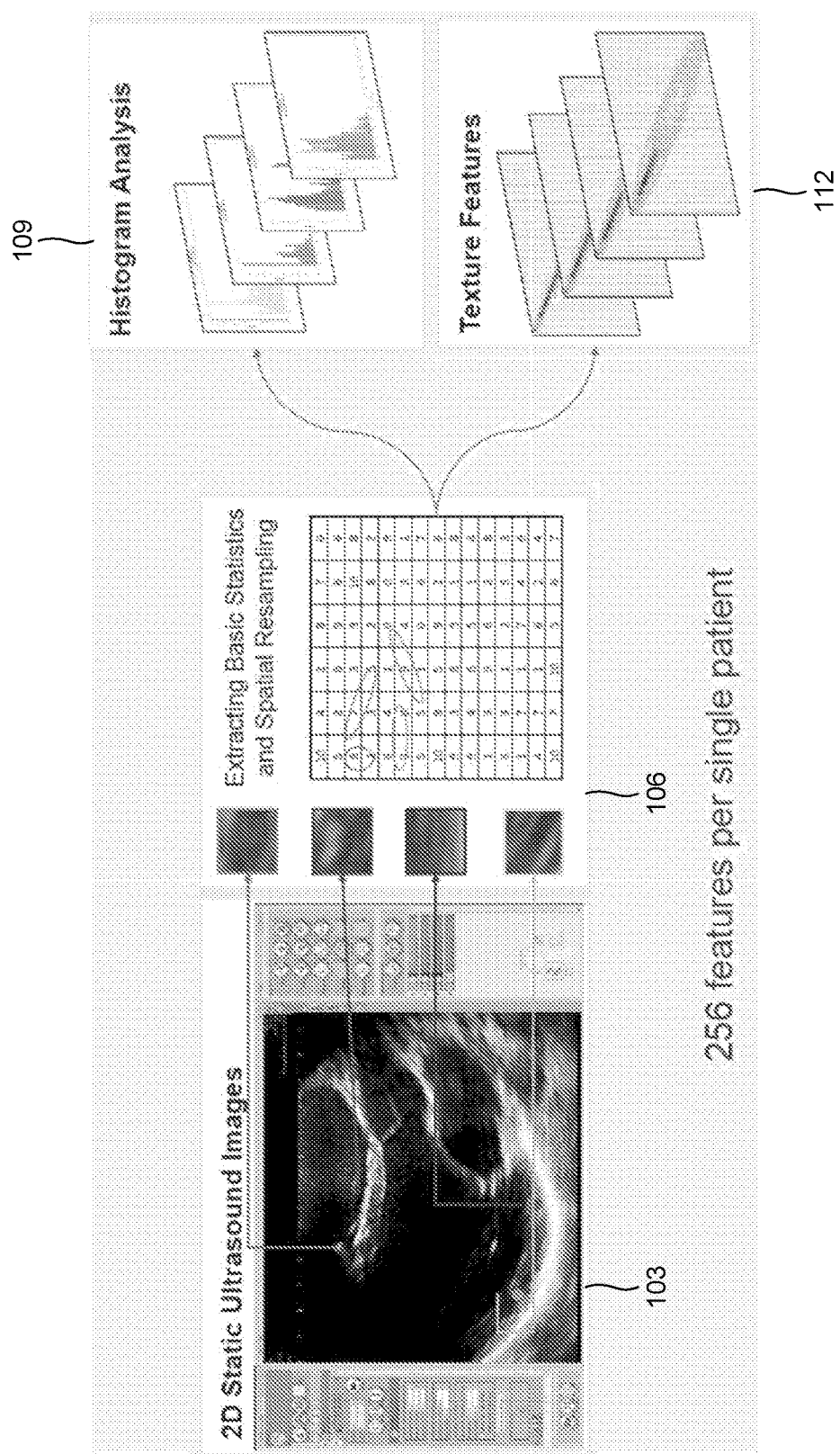
FIG. 1 is an example of an ultrasound image and extracted basic statistic and spatial resampling variables from the ultrasound image in accordance with various embodiments of the present disclosure.

Aspects of the present disclosure are related to a myocardial imaging technique called myocardial ultrasonic fingerprinting that utilizes a radiomics-based approach and high-throughput computing on static cardiac ultrasound images.

In one aspect, among others, a system comprises at least one computing device and at least one application executable on the at least one computing device. When executed, the at least one application causes the at least one computing device to at least extract a plurality of radiomic features from an ultrasound image associated with a patient, determine one or more myocardial characteristics by applying the extracted plurality of radiomic features to one or more phenotyping models, and interpret a clinical significance associated with the patient based at least in part on the one or more myocardial characteristics and the extracted plurality of radiomic features.

In various aspects, among others, the ultrasound image comprises a plurality of ultrasound images. In various aspects, among others, the ultrasound image is a static image. In various aspects, among others, when executed, the at least one application causes the at least one computing device to at least identify a selection of a region of interest in the ultrasound image and the plurality of radiomics features are extracted within the region of interest.

In various aspects, among others, the radiomic features are extracted from a pixel-based pattern in the ultrasound image. In various aspects, among others, when executed, the at least one application further causes the at least one computing device to at least identify one or more myocardial textures based at in part on a clustering of the extracted plurality of radiomic features. In various aspects, among others, the ultrasound image is of a region of a heart. In various aspects, among others, the clinical significance is further based at least in part on matching the plurality of radiomic features to a patient cluster.

In various aspects, among others, the clinical significance is further based at least in part on matching the radiomic features to a gradient of a patient cluster. In various aspects, among others, the clinical significance comprises at least one of a ventricular malformation, a risk of advanced heart failure, myocardial fibrosis, one or more cardiac malignancies, or heart valve deterioration. In various aspects, among others, the one or more phenotyping models comprise at least one of a neural network classifier, a support vector machine (SVM) classifier, or a deep learning classifier. In various aspects, among others, when executed, the at least one application further causes the at least one computing device to at least select a portion of the plurality of radiomics features, select at least one of the one or more phenotyping models based at least in part on the portion of the plurality of radiomics features, and determine the one or more myocardial characteristics is based at least in part on the portion of the plurality of radiomics features and the at least one of the one or more phenotyping models.

In one aspect, among others, a method, comprises extracting, via at least one computing device, a plurality of radiomic features from an ultrasound image associated with a person, identifying, via the at least one computing device, one or more myocardial textures by applying the extracted plurality of radiomic features to at least one phenotyping model, and determining, via the at least one computing device, at least one condition associated with the person based at least in part on the one or more myocardial textures and the extracted plurality of radiomic features.

In various aspects, among others the method further comprising: comparing, via the at least one computing device, the one or more myocardial textures to at least one phenotype cluster for at least one known condition; and determining the at least one condition is based at least in part on the one or more myocardial textures being matched with one or more of the at least one phenotype cluster.

In various aspect, among others, the method further comprises obtaining, via at least one computing device, the ultrasound image from an ultrasound capturing device in data communication with the at least one computing device. In various aspect, among others, extracting the plurality of radiomic features from the ultrasound image further comprises detecting pixel-based patterns in the ultrasound image. In various aspect, among others, the method further comprises identifying, via the at least one computing device, at least one selected region of interest in the ultrasound image, wherein the plurality of radiomic features are extracted from the at least one selected region of interest in the ultrasound image.

In various aspect, among others, the at least one condition comprises at least one of a ventricular malformation, a risk of advanced heart failure, myocardial fibrosis, one or more cardiac malignancies, or heart valve deterioration. In various aspect, among others, the one or more phenotyping models comprise at least one of a neural network classifier, a support vector machine (SVM) classifier, or a deep learning classifier. In various aspect, among others, the ultrasound image comprises a static two-dimensional cardiac ultrasound image.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

DETAILED DESCRIPTION

Disclosed herein are various embodiments related to characterizing pathological myocardial tissue using computational processes to acquire, process, and visualize data. In particular, systems and methods of the present disclosure relate to a myocardial imaging technique called myocardial ultrasonic fingerprinting that utilizes a radiomics-based approach and high-throughput computing on static cardiac ultrasound images. The technique allows for the extraction of pixel-based information from noisy multidimensional static images and isolates quantitative features of myocardial tissue. In addition, machine learning techniques accompany the data analysis to enhance the signal-to-noise ratio from complex multidimensional data. In this manner, the fingerprinting technique of the present disclosure elucidates numerous features that can serve as predictors of cardiovascular pathology as well as prognostic indicators measuring treatment response.

Cardiovascular disease accounts for one in every four deaths in the United States—approximately 610,000 people every year, according to the Centers for Disease Control. Tissue characterization of myocardial pathology has been an area of intense research and development due to the rising incidence of cardiovascular conditions and the growing geriatric population. Many noninvasive imaging techniques are used to associate myocardial imaging features with pathological assessments. While cardiac ultrasound is considered the first-line noninvasive diagnostic imaging tool to assess myocardial function, ultrasound images do not always display accurate tissue characterization. This has mainly been due to variant intensities that affect the signal-to-noise ratio, which in turn affects the quality of images from echocardiography.

Cardiac ultrasound imaging is considered the most accessible and first-line imaging tool with accurate assessment of myocardial function and flow dynamics. Furthermore, radiomics is a method that extracts large number of features from radiographic medical images using data-characterization algorithms. These features, termed radiomic features, have the potential to uncover disease characteristics that fail to be appreciated by the naked eye. Groups have utilized the radiomics approach to analyze ultrasound images of breast tissue and found the radiomics approach could differentiate between different types of cancers. Moreover, other groups have analyzed Computed Tomography (CT) and myocardial perfusion Singly Photon Emission Control Tomography (SPECT) images for cardiac purposes using a radiomics-based approach. Typical myocardial texture is visually distinguishable with ultrasound images. However, image quality and texture of ultrasound images may vary significantly. The variance of image quality and texture of ultrasound images is induced by different factors including, for example, patient factors, existence of a good acoustic window, machine settings, and skill of sonographers, thereby preventing reproducible quantitative myocardial texture analysis.

According to various embodiments, myocardial ultrasonic fingerprinting characterizes pathological myocardial tissue using cutting-edge computational processes to acquire, process, and visualize data. Myocardial ultrasonic fingerprinting uses multiple material properties and a radiomics-based approach to parameter mining that identifies pathological changes earlier than traditional qualitative imaging. The radiomics-based approach improves the predictive accuracy of the diagnosis, and the machine learning techniques that accompany the data analysis provide a method to enhance the signal-to-noise ratio from complex, multidimensional data. The pathological features that the present disclosure could detect include left ventricular (LV) malformations, risk of advanced heart failure, and myocardial fibrosis. The technology could also potentially detect cardiac malignancies and heart valve deterioration.

According to various embodiments of the present disclosure, radiomic-based myocardial ultrasonic fingerprinting improves traditional tissue imaging techniques using echocardiography and provides a reliable prediction of cardiological issues. The disclosed method is more precise than other tissue imaging techniques because radiomic-based myocardial ultrasonic fingerprinting allows for extraction of information from noisy multidimensional medical images and identifies quantitative features of myocardial tissue from static cardiac ultrasound images.

According to various embodiments of the present disclosure, the radiomic-based myocardial ultrasonic fingerprinting further improves traditional myocardial tissue characterizations by extracting maximal information from standard-of-care images using high-throughput computing. Compared with other conventional approaches, radiomic-based fingerprinting can extract at least sixty-four (64) distinct variables from any predefined region of a cardiac ultrasonic image, or at least 256 distinct variables from a single patient. Subsequently, in view of traditional methods of characterizations requiring sonographers, texture-based machine learning phenotyping is applied to the extracted variables to identify patient clusters and thereby diagnose various pathological conditions including, but not limited to, left ventricular (LV) malformations, risk of advanced heart failure, myocardial fibrosis, cancer taxonomy, predictive therapeutic response, gene expression, and/or other conditions. Furthermore, according to various embodiments, the present disclosure allows for earlier identification of pathological cardiovascular changes than compared to traditional qualitative imaging techniques, thereby improving diagnostic, prognostic, and predictive accuracy.

According to various embodiments of the present disclosure, radiomics-based myocardial ultrasonic fingerprinting further improves on traditional approaches of myocardial tissue characterization by identifying myocardial fibrosis using radiomic-based clustering. Although this feature may be extracted from static images, similar accuracy is achieved as full frame derived global longitudinal strain (GLS) values for identifying myocardial fibrosis. Thus, radiomic-based fingerprinting can extract important image features. Therefore, excellent diagnostic accuracy can be achieved from the combination of GLS and radiomic features.

According to various embodiments, radiomic-based myocardial ultrasonic fingerprinting improves traditional approaches of myocardial tissue characterization by being able to reliably predict cardiological issues without requiring the storage, processing, and use of dense movie files for analysis. The radiomics-based fingerprinting approach may be applied to static cardiac ultrasound images. As a result, data storage usage is greatly reduced, thereby significantly reducing costs to users.

Reference will now be made in detail to the description of the embodiments as illustrated in the drawings, wherein like reference numbers indicate like parts throughout the several views.

Turning to FIG. 1, shown is an example of a two-dimensional (2D) ultrasound image 103 and the information that may be extracted from the 2D ultrasound image 103, according to various embodiments of the present disclosure. From the 2D ultrasound image 103, quantitative radiomic texture indices are extracted in the form of basic statistics and spatial resampling variables 106. In this example, multiple (e.g., 256) radiomic texture indices may be extracted from an image for a single patient. From the extracted basic statistics and spatial resampling variables 106, histogram analysis 109 may be performed and texture features 112 may be characterized. Those texture features can include Gray Level Co-occurrence Matrix (GLCM), Gray Level Zone Length Matrix (GLZLM), Gray Level Run Length Matrix (GLRLM), Neighborhood Grey Level Different Matrix (NGDLDM), and/or other type of texture feature as can be appreciated. Each feature (e.g., matrix) carries unique information. For example, GLCM takes into account the arrangements of pairs of voxels to calculate textural indices. GLZLM provides information on the size of homogeneous zones for each grey-level. GLRLM gives the size of homogeneous runs for each grey level. NGLDM corresponds to the difference of grey-level between one voxel and its neighbors.

Figure 2A:
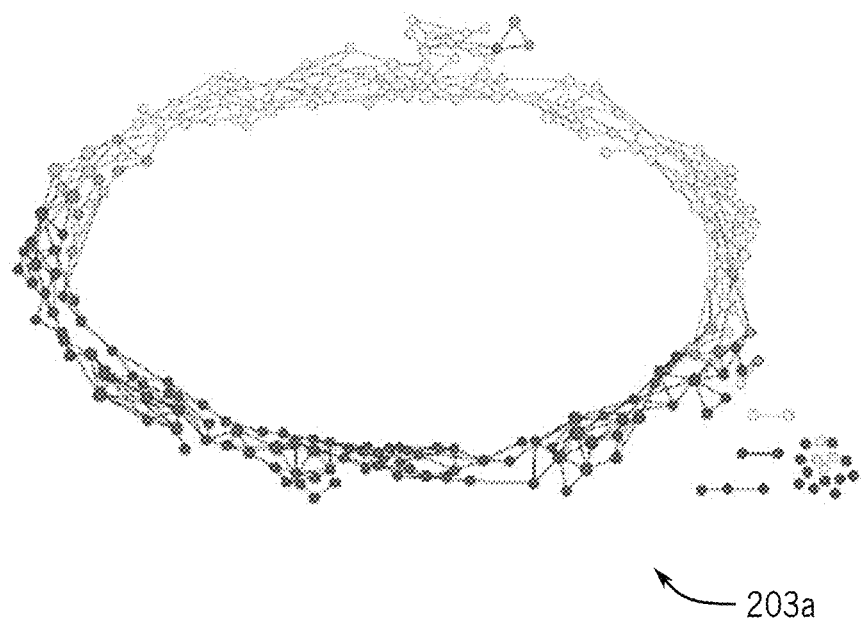
FIGS. 2A-2B are example of patient cluster models in accordance with various embodiments of the present disclosure.
Figure 2B:
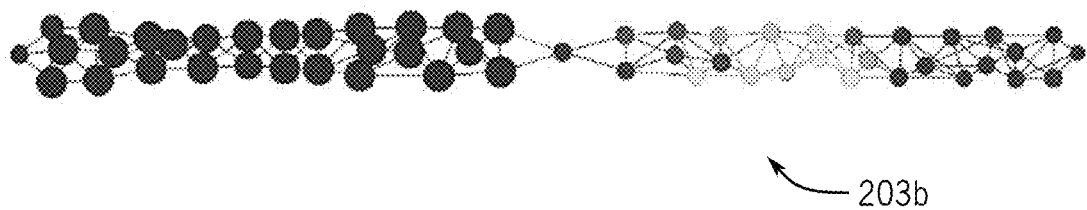

In FIGS. 2A and 2B, shown are examples of patient cluster mappings 203 (e.g., 203a, 203b) for a cardiac issue, according to various embodiments of the present disclosure. Once basic statistics and spatial resampling variables 106 (FIG. 1) are extracted from a 2D ultrasound image 103 (FIG. 1), the myocardial ultrasonic fingerprinting application 815 (FIG. 8) matches the extracted variables to a patient cluster mapping 203. The patient cluster mappings 203 are identified using unsupervised machine learning techniques where similar patients are aggregated in nodes that are close to each other. In particular, the patient cluster mappings 203 can be identified using a patient similarly analysis such as, for example, a topological data analysis, as shown in FIGS. 2A and 2B. The geometry identifies groups of similar patients and their significance is understood by colorizing clinical features and outcome that have not been part of the initial model building.

Figure 3:
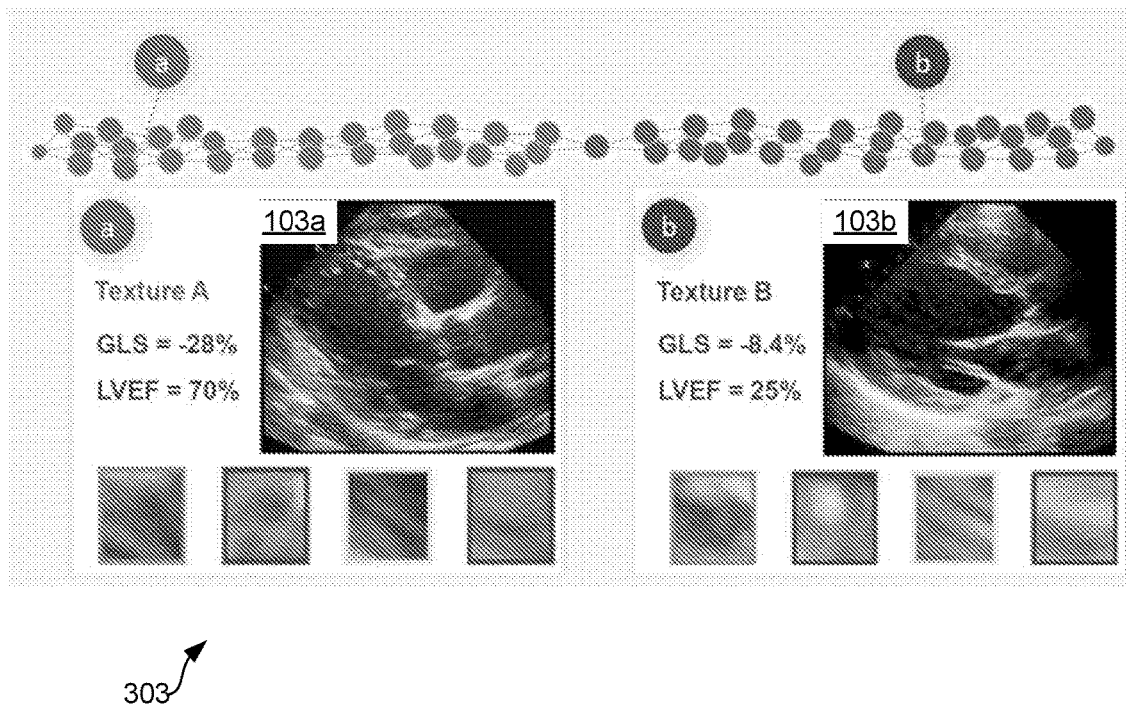
FIG. 3 is an example of patient textures and texture-based phenotyping of left ventricular (LV) function in accordance with various embodiments of the present disclosure.

In FIG. 3, shown is an example of texture-based phenotyping 300 for left ventricle function and a table 306 showing a comparison between texture A and B, according to various embodiments of the present disclosure. The texture-based phenotyping for the left ventricle function can identify different texture features, such as GLS and Left Ventricular Ejection Fraction (LVEF), from pixel-based patterns in a 2D cardiac ultrasonic image 103 (e.g., 103a, 103b), thereby identifying quantitative features of myocardial tissue with more predictive accuracy than conventional methods, and allowing for identification of pathological cardiovascular changes earlier than traditional qualitative imaging. The texture-based phenotyping of LV function as shown in FIG. 3 may also be used to perform a comparison between textures 306 to aid in identifying various cardiac conditions.

Figure 4A:
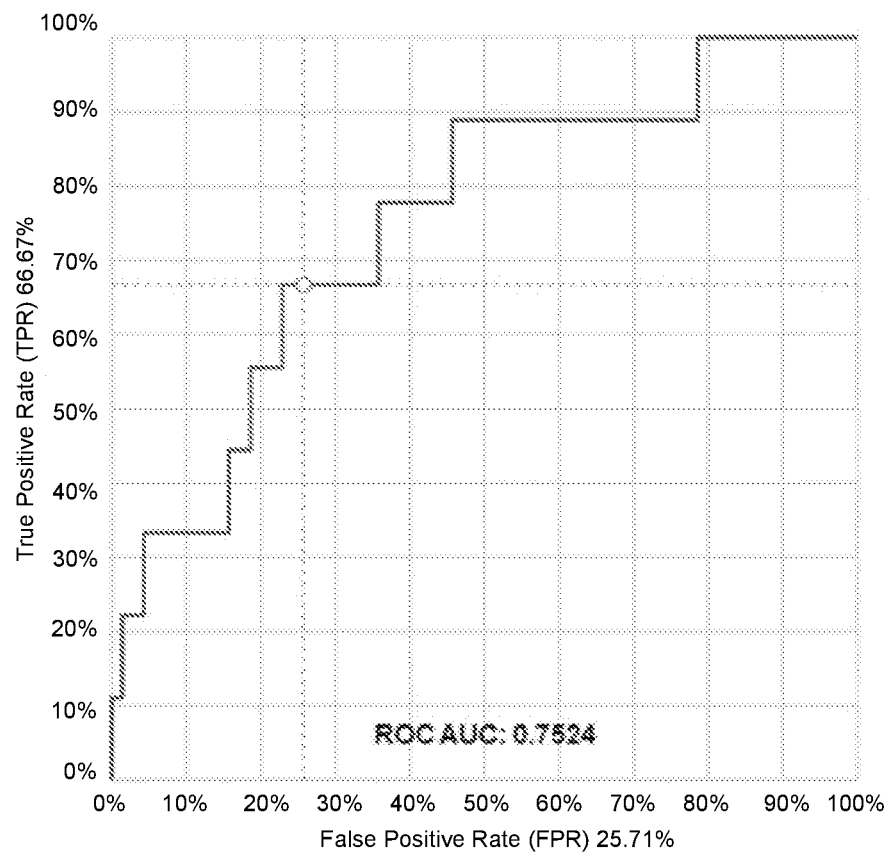
FIGS. 4A-4C are plots associated with automated supervised machine learning prediction for different prognosis in accordance with various embodiments of the present disclosure.
Figure 4B:
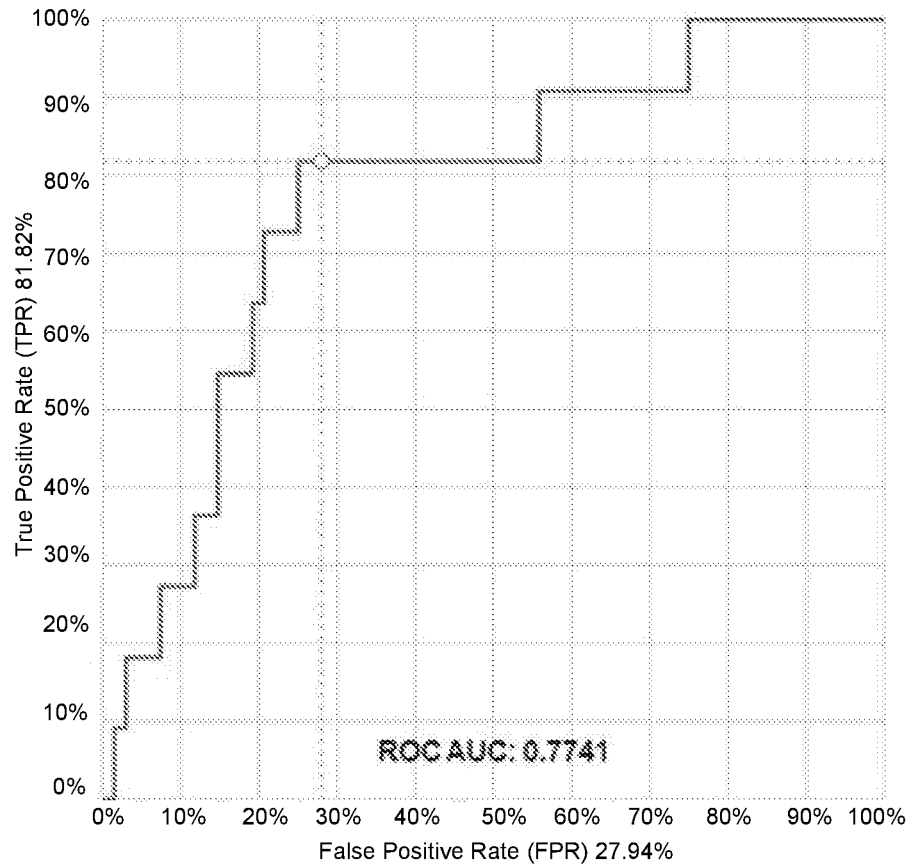

Turning to FIGS. 4A-4B, shown are example plots illustrating automated supervised machine learning prediction measurement for three representative cardiac features.

Figure 4C:
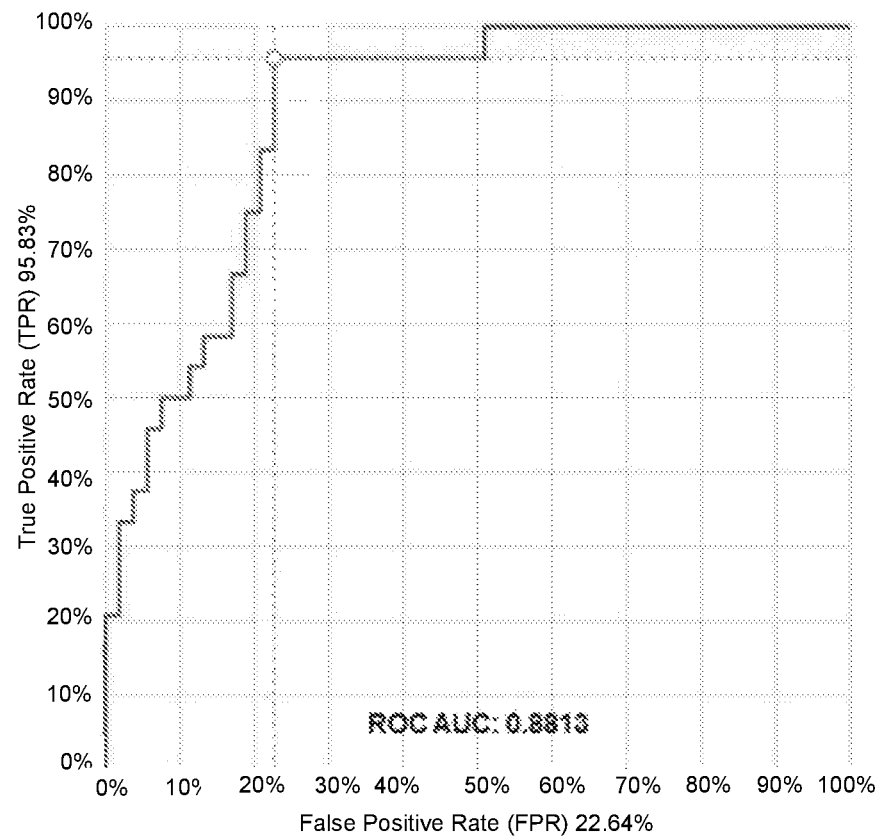

According to various embodiments, FIG. 4A illustrates a plot 403 associated with LV hypertrophy, FIG. 4B illustrates a plot 406 associated with LVEF 406, and FIG. 4C illustrates a plot 409 associated with GLS. The automated supervised machine learning prediction of the present disclosure, and as shown in FIGS. 4A-4C, provides an evaluation metric for various cardiac features. In addition, the automated supervised machine learning prediction allows for monitoring of sensitivity, specificity, and likelihood ratio (LR) for various cardiac texture.

Figure 5A:
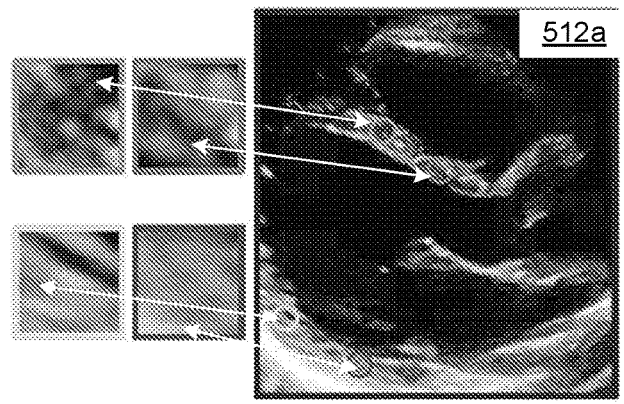
FIGS. 5A-5C are examples of identified myocardial fibrosis from textures and an example of classification of high-risk or low-risk myocardium clusters in accordance with various embodiments of the present disclosure.
Figure 5A:
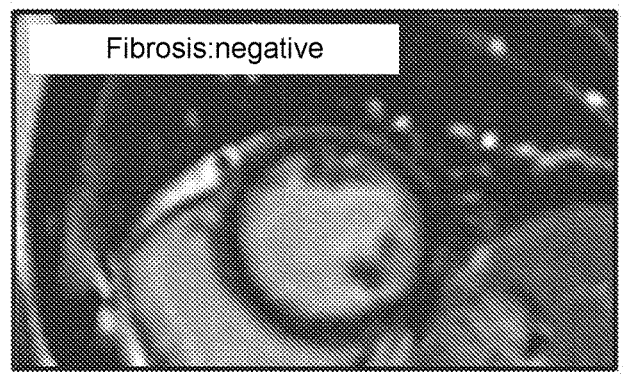
Figure 5B:
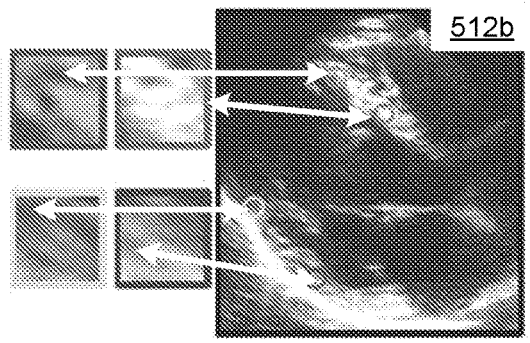
Figure 5B:
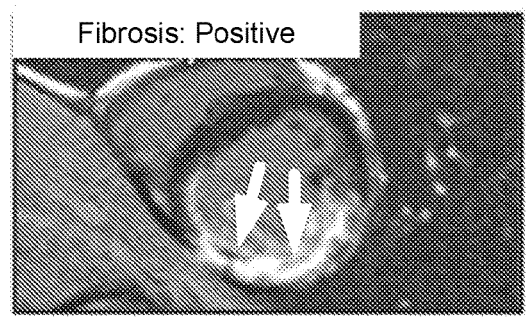
Figure 5C:
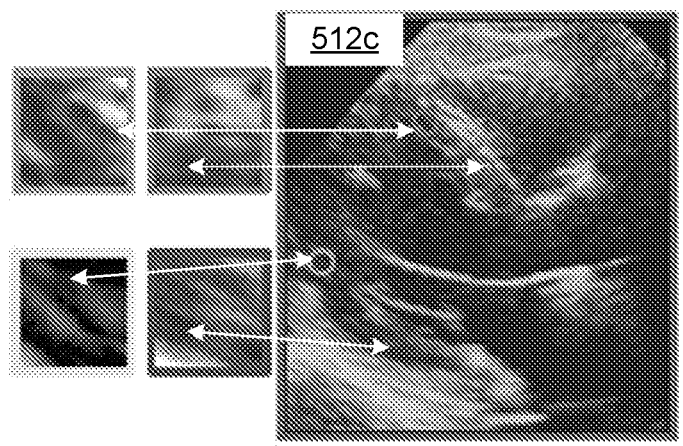
Figure 5C:
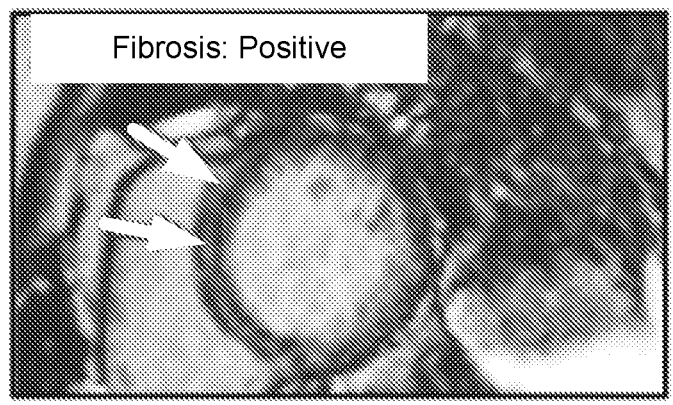

In FIGS. 5A-5C shown are examples of myocardial fibrosis textures 503 (e.g., 503a, 503b, 503c) for different patients, according to various embodiments of the present disclosure. In particular, FIGS. 5A-5C illustrate static cardiac ultrasound images 512 (e.g., 512a, 512b, 512c) of different patients and illustrate different conditions corresponding to normal myocardium, myocardial infarction, and cardiomyopathy. According to various embodiment, the myocardial ultrasonic fingerprinting application 815 (FIG. 8) can be trained to identify negative or positive myocardial fibrosis textures through radiomic-based clustering of a static cardiac ultrasound image 512. Although these features are extracted from a static cardiac ultrasound image 512, similar accuracy as full-frame GLS values for identifying myocardial fibrosis is achieved. Thus, exemplifying excellent diagnostic accuracy from the combination of GLS and radiomic features. Therefore, radiomic-based fingerprinting can extract important hidden image features that are tightly associated with cardiac disease conditions.

Example 1

Figure 6:
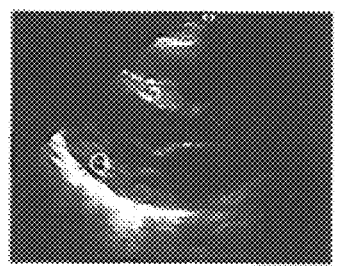
FIG. 6 is an example of a graded patient cluster separated into high risk myocardium textures and low-risk myocardium textures in accordance with various embodiments of the present disclosure.
Figure 6:
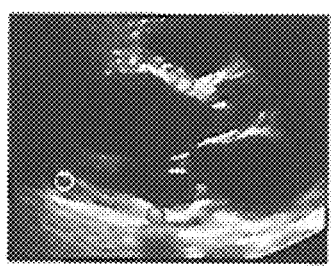
Figure 6:
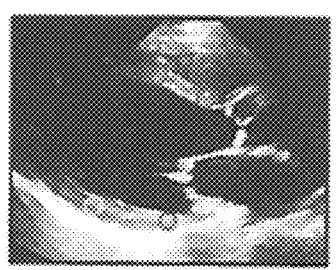
Figure 6:
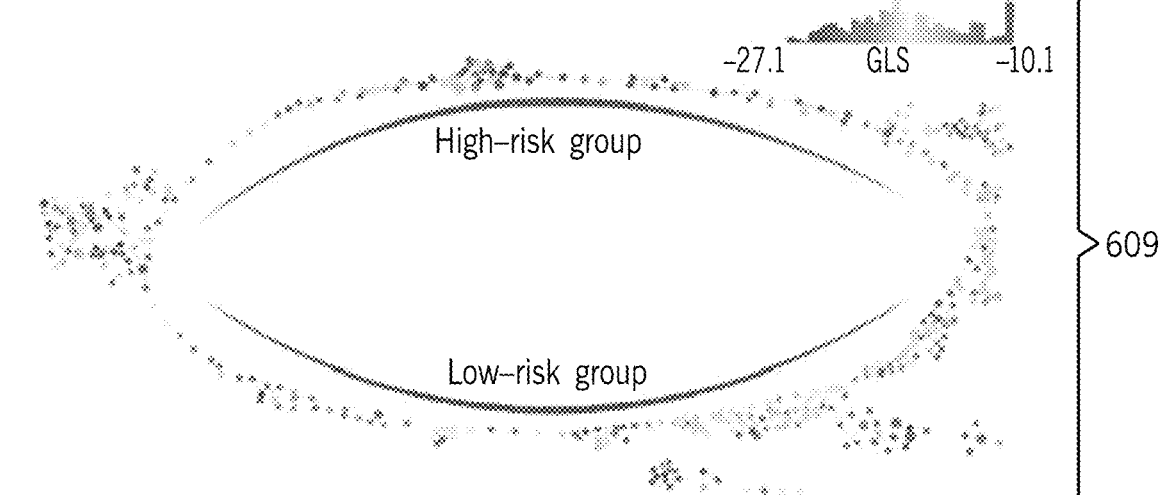
Figure 6:
Figure 6:
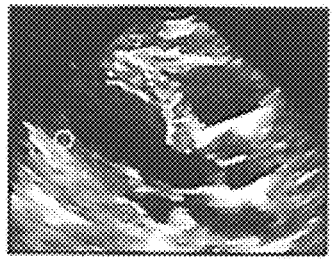
Figure 6:

Preliminary evidence and proof-of-concept was demonstrated in a recent investigation involving two hundred fifty-six (256) radiomic texture indices from images taken from 446 patients. The radiomic data was compared with conventional echocardiography and 2D speckle tracking derived global longitudinal strain. In a subgroup of forty patients undergoing cardiac magnetic resonance (CMR), high-risk fingerprint was subsequently assessed in total 160 left ventricular (LV) segments for predicting the presence of myocardial fibrosis as defined by late gadolinium-enhanced CMR. As shown in FIG. 6, topological data analysis clustered the patients with high and low-risk myocardial fingerprint in an unsupervised manner.

The high-risk pathological features were associated with conventional markers of LV remodeling including LV end-diastolic and systolic volumes, ejection fraction, and impaired global longitudinal strain. Furthermore, the high-risk fingerprint predicted presence of advanced heart failure (ACC/AHA stage≥C) and symptoms (NYHA class≥III). In patients undergoing CMR, the high-risk fingerprint was an independent predictor of fibrosis, and adding fingerprint information to global longitudinal strain improved prediction of myocardial fibrosis. Taken together, these results indicated that radiomic-based cardiac ultrasound fingerprinting identifies high-risk features associated with LV remodeling in early and advanced clinical stages of heart failure.

FIG. 6 illustrates an example of classification of various cardiac textures based on the above experiment according with high-risk myocardium 603 and low-risk myocardium 606 within a patient cluster 609 based on phenotyping, according to various embodiments of the present disclosure. Although the classification of FIG. 6 identifies two clusters (e.g., high risk, low risk), extracted radiomic-based fingerprinting may be classified with any number of graded patient clusters to identify a variety of clinically significant indications.

Figure 7:
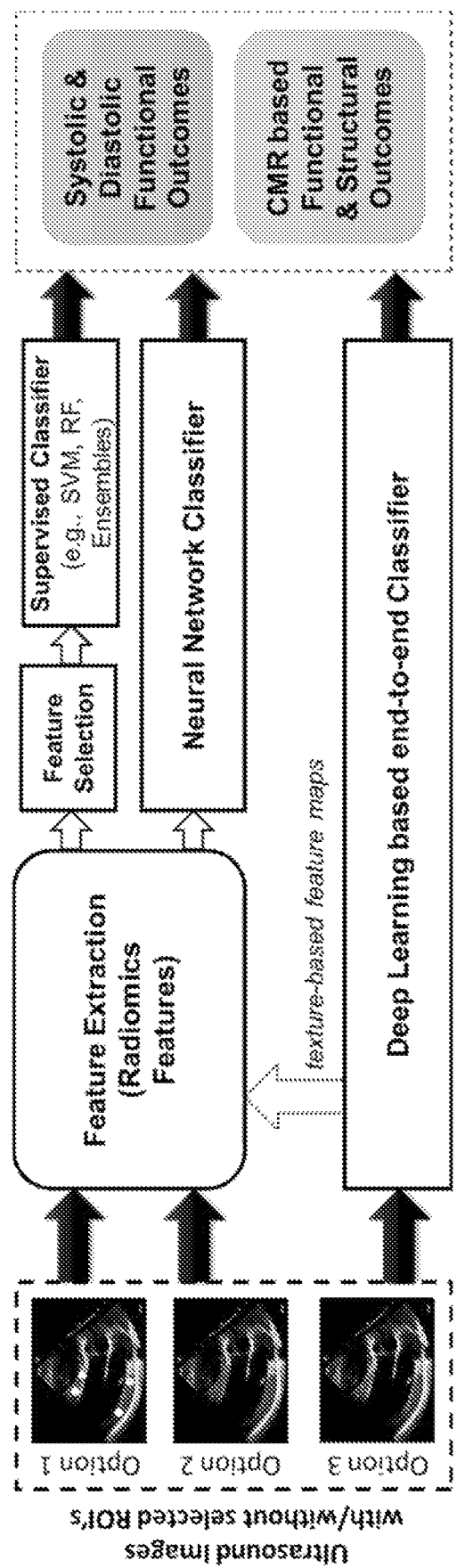
FIG. 7 is a schematic diagram illustrating associated with the machine learning pipeline for characterizing myocardial tissue based on extracted features from ultrasound images in accordance with various embodiments of the present disclosure.

Turning now to FIG. 7, shown is a sample schematic associated with the machine learning pipeline for cardiac ultrasonic fingerprinting, according to various embodiments of the present disclosure. In particular, FIG. 7 relates to various techniques that can be used to generate myocardial ultrasonic fingerprints that can be used to identify cardiac characteristics that can be used to diagnosis and treat patients.

In various embodiments, features associated with the obtained images can be extracted from static cardiac ultrasound images 103, 512. In some embodiments, the features can be extracted based on selected regions of interest within the image. In other embodiments, the features can be extracted without a selection of a region of interest. The features can correspond to quantitative radiomic texture indices are extracted in the form of basic statistics and spatial resampling variables.

Figure 8:
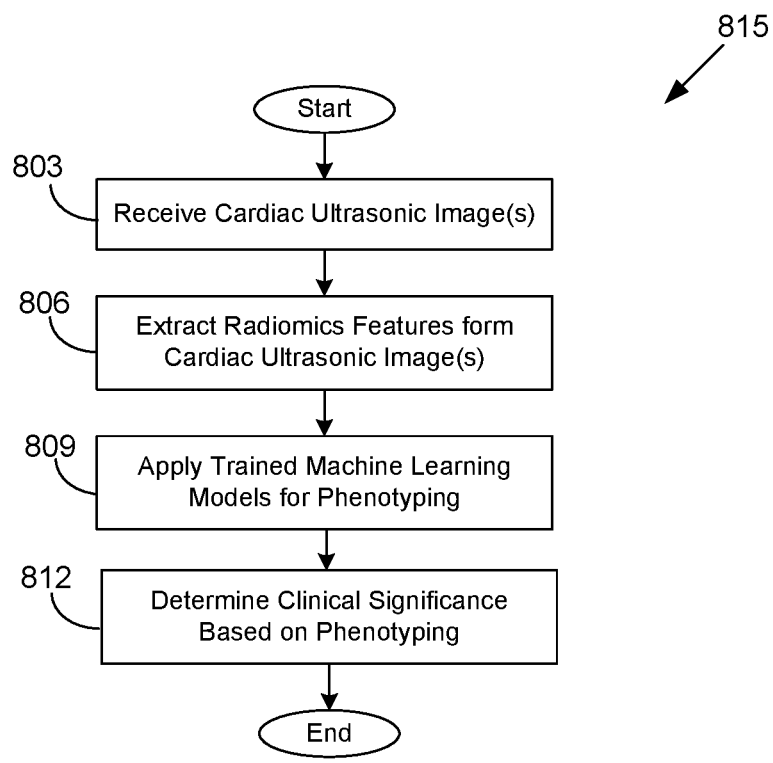
FIG. 8 is a flowchart illustrating one example of functionality implemented as portions of the myocardial ultrasound fingerprinting application executed in a computing environment, in accordance to various embodiments of the present disclosure.

The features can be applied to trained machine learning models in the form of deep learning-based classifiers, supervised classifiers, and neural network classifiers for high-throughput myocardial feature phenotyping. Accordingly, the trained models of the present disclosure can map the extracted features to various myocardial feature phenotypes. In particular, the analysis of the extracted features from the images and application of the extracted features with respect to the trained models can be used to identify various cardiac characteristics including, for example, systolic functional characteristics, diastolic functional characteristics, cardiac magnetic resonance (CMR) based functional characteristics, CMR based structural characteristics, and/or other cardiac characteristics Turning now to FIG. 8, shown is an example of a flowchart illustrating one example of the operation of a portion of the myocardial ultrasonic fingerprinting application 915 (FIG. 9) executed in a computing environment according to various embodiments of the present disclosure. It is understood that the flowchart of FIG. 8 provides merely an example of the many different types of functional arrangements that may be employed to implement the operation of the portion of the myocardial ultrasonic fingerprinting application 915 (FIG. 9) as described herein. As an alternative, the flowchart of FIG. 8 may be viewed as depicting an example of elements of a method implemented in the computing environment according to one or more embodiments.

Beginning with box 803, the myocardial ultrasonic fingerprinting application 815 (FIG. 8) obtains one or more cardiac ultrasound images 103, 512 of a patient. For example, the myocardial ultrasonic fingerprinting application 815 could receive a single 2D cardiac ultrasound image 103 (FIG. 1) of a region of the heart. As another example, the myocardial ultrasonic fingerprinting application 815 could receive multiple images 103, 512 of one or more regions of the heart. Upon receiving the images 103, 512, the myocardial ultrasonic fingerprinting application 815 may extract and temporarily store all of the images for further processing.

Moving on to box 806, the myocardial ultrasonic fingerprinting application 815 extracts radiomics features from cardiac ultrasonic images 103, 512. For example, the myocardial ultrasonic fingerprinting application 815 can identify pixel-based patterns from a 2D cardiac ultrasound image that cannot be appreciated by the human eye. The myocardial ultrasonic fingerprinting application 815 can extract radiomic features from the 2D cardiac ultrasound image 103, 512 in the form of basic statistics and spatial resampling variables 106 (FIG. 1). As another example, the myocardial ultrasonic fingerprinting application 815 (FIG. 8) can extract radiomic features 106, 109, 112 (FIG. 1) from a plurality of 2D cardiac ultrasound images 103 (FIG. 1) and use the extracted radiomic features to perform histogram analysis 109 and characterize certain myocardial texture features 112 (FIG. 1) despite variations in quality and texture of 2D cardiac ultrasound images 103 (FIG. 1). In some embodiments, the extracted features may correspond to selected regions of interest. For example, a user may select various regions of interest in a given image that are to be analyzed. In other embodiments, there are no selected regions of interest and the image is analyzed as a whole without a selection of one or more regions of interest.

Proceeding to box 809, the myocardial ultrasonic fingerprinting application 815 (FIG. 8) can apply the extracted radiomic features 106, 109, 112 (FIG. 1) to trained machine learning models for myocardial phenotyping. In some embodiments, the myocardial ultrasonic fingerprinting application 815 can apply the extracted radiomic features 106, 109, 112 (FIG. 1) to selected machine learning phenotyping models and match the phenotype to a patient cluster 203 (FIG. 2) for an identified cardiac issue. As another example, myocardial ultrasonic fingerprinting application 815 (FIG. 8) can apply the extracted radiomic features 106, 109, 112 (FIG. 1) to selected machine learning phenotyping models and match the phenotype to at least one of a plurality of grades of patient clusters 609 (FIG. 6) for multiple cardiac issues or for different grades of a particular cardiac issue.

Moving on to box 812, the myocardial ultrasonic fingerprinting application 815 can identify phenotypic features based at least in part on extracted radiomic features 106, 109, 112 (FIG. 1) of a 2D cardiac ultrasound image 103 and interpret the clinical significance (e.g., left ventricular (LV) malformations, risk of advanced heart failure, myocardial fibrosis, cardiac malignancies, heart valve deterioration, etc.). In another example, the myocardial ultrasonic fingerprinting application 815 (FIG. 8) can interpret clinical significance based at least in part on the 2D cardiac ultrasound image's 103 match to a patient cluster 203 or at least one of plurality of different grades of patient clusters 609. As another example, the extracted phenotypic features from the 2D cardiac ultrasound images can be used in bioinformatics platform analysis model to identify the group the patient belongs to.

Thereafter, the process proceeds to completion.

Figure 9:
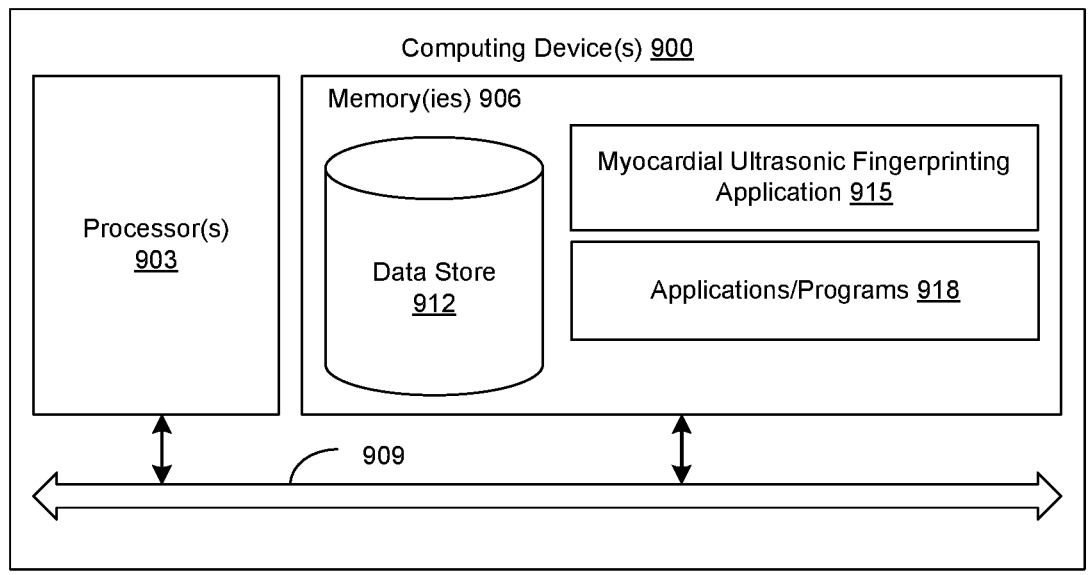
FIG. 9 is a schematic block diagram that provides one example illustration of a computing environment according to various embodiments of the present disclosure.

With reference now to FIG. 9, shown is one example of at least one computing device 900 (e.g., an interfacing device, central server, server, or other network device) that performs various functions of the myocardial ultrasonic fingerprinting algorithms in accordance with various embodiments of the present disclosure. Each computing device 900 includes at least one processor circuit, for example, having a processor 903 and a memory 906, both of which are coupled to a local interface 809. To this end, each computing device 900 may be implemented using one or more circuits, one or more microprocessors, microcontrollers, application specific integrated circuits, dedicated hardware, digital signal processors, microcomputers, central processing units, field programmable gate arrays, programmable logic devices, state machines, or any combination thereof. The local interface 909 may comprise, for example, a data bus with an accompanying address/control bus or other bus structure as can be appreciated. Each computing device 900 can include a display for rendering of generated graphics such as, e.g., a user interface and an input interface such, e.g., a keypad or touch screen to allow for user input. In addition, each computing device 800 can include communication interfaces (not shown) that allows each computing device 900 to communicatively couple with other communication devices. The communication interfaces may include one or more wireless connection(s) such as, e.g., Bluetooth or other radio frequency (RF) connection and/or one or more wired connection(s).

Stored in the memory 906 are both data and several components that are executable by the processor 903. In particular, stored in the memory 906 and executable by the processor 903 is the myocardial ultrasonic fingerprinting application 915, and/or other applications 918. Also stored in the memory 903 may be a data store 912 and other data. It is understood that there may be other applications that are stored in the memory 906 and are executable by the processor 903 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Delphi®, Flash®, LabVIEW® or other programming languages.

A number of software components are stored in the memory 906 and are executable by the processor 903. In this respect, the term "executable" means a program file that is in a form that can ultimately be run by the processor 903. Examples of executable programs may be, for example, a compiled program that can be translated into machine code in a format that can be loaded into a random access portion of the memory 906 and run by the processor 903, source code that may be expressed in proper format such as object code that is capable of being loaded into a random access portion of the memory 906 and executed by the processor 903, or source code that may be interpreted by another executable program to generate instructions in a random access portion of the memory 906 to be executed by the processor 903, etc. An executable program may be stored in any portion or component of the memory 906 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 906 is defined herein as including both volatile and nonvolatile memory and data storage components. Volatile components are those that do not retain data values upon loss of power. Nonvolatile components are those that retain data upon a loss of power. Thus, the memory 806 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 903 may represent multiple processors 903 and the memory 906 may represent multiple memories 906 that operate in parallel processing circuits, respectively. In such a case, the local interface 909 may be an appropriate network that facilitates communication between any two of the multiple processors 903, between any processor 903 and any of the memories 906, or between any two of the memories 906, etc. The local interface 909 may comprise additional systems designed to coordinate this communication, including, for example, performing load balancing. The processor 903 may be of electrical or of some other available construction.

Although the myocardial ultrasonic fingerprinting application 915, other application(s) 918, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Also, any logic or application described herein, including the myocardial ultrasonic fingerprinting application 915 and/or application(s) 918, that comprises software or code can be embodied in any non-transitory computer-readable medium for use by or in connection with an instruction execution system such as, for example, a processor 803 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Example 2

A rise in cardiovascular risk factors, improved survival rate from ischemic heart disease, and population-ageing have contributed to the increasing global burden of heart failure. An important step to prevent the progression of heart failure includes early detection of left ventricular (LV) remodeling—a process driven by architectural cellular and interstitial changes in the myocardium and identified clinically as global changes in LV size, geometry, and function. Studies have shown that the degree of LV remodeling has a strong correlation with the impact of particular drugs or device therapies as well as with clinical outcomes.

Recent advancements in cardiac magnetic resonance (CMR) have revealed that myocardial tissue imaging characteristics alter under various cardiac conditions which reflect structural LV remodeling, including fibrosis, increased extracellular volume, and altered fibre orientation. Cardiac ultrasound is not currently utilized clinically for myocardial tissue characterization although previous studies have reported that the intensity of the ultrasound backscatter is related to the physical properties of the myocardium and is influenced by tissue components (e.g., collagen, water, fat). Moreover, there has been limited information regarding the specific application of texture-based analysis for cardiac ultrasound imaging.

The recent developments in image analysis and novel bioinformatics approaches have augmented methods that can extract information from the texture in a still image. The application of such texture-based image analysis has been increasingly utilized as a key function in various image processing applications such as automated inspection, document processing, radiology image processing, and content-based image retrieval. Such techniques may also have direct relevance for cardiac ultrasound techniques like speckle tracking echocardiography where myocardial motion is analyzed using frame-by-frame tracking of natural acoustic markers (often referred in literature as "speckles", "patterns", or "fingerprints"). A functional unit (kernel) of speckles generated from ultrasound-tissue interactions (e.g., reflections, interference, and scattering) is unique, allowing software to track itself during the entire cardiac cycle. Thus, an ultrasound texture of myocardium may carry unique and specific information of the indexed myocardium.

According to various embodiments, the present disclosure presents the development and validation of a novel approach that combines the texture-based informatics of myocardium with machine learning techniques. First, texture-based tissue features are extracted from still ultrasound images and the association of texture feature-based patient phenotypes with LV remodeling are identified. Subsequently, the value of texture-based supervised machine learning models in predicting LV systolic dysfunction and the presence of myocardial fibrosis in a remodeled LV is illustrated.

Materials and Methods

Study Participants

This study consisted of three parts. The detailed study design is presented in FIG. 10.

Figure 10:
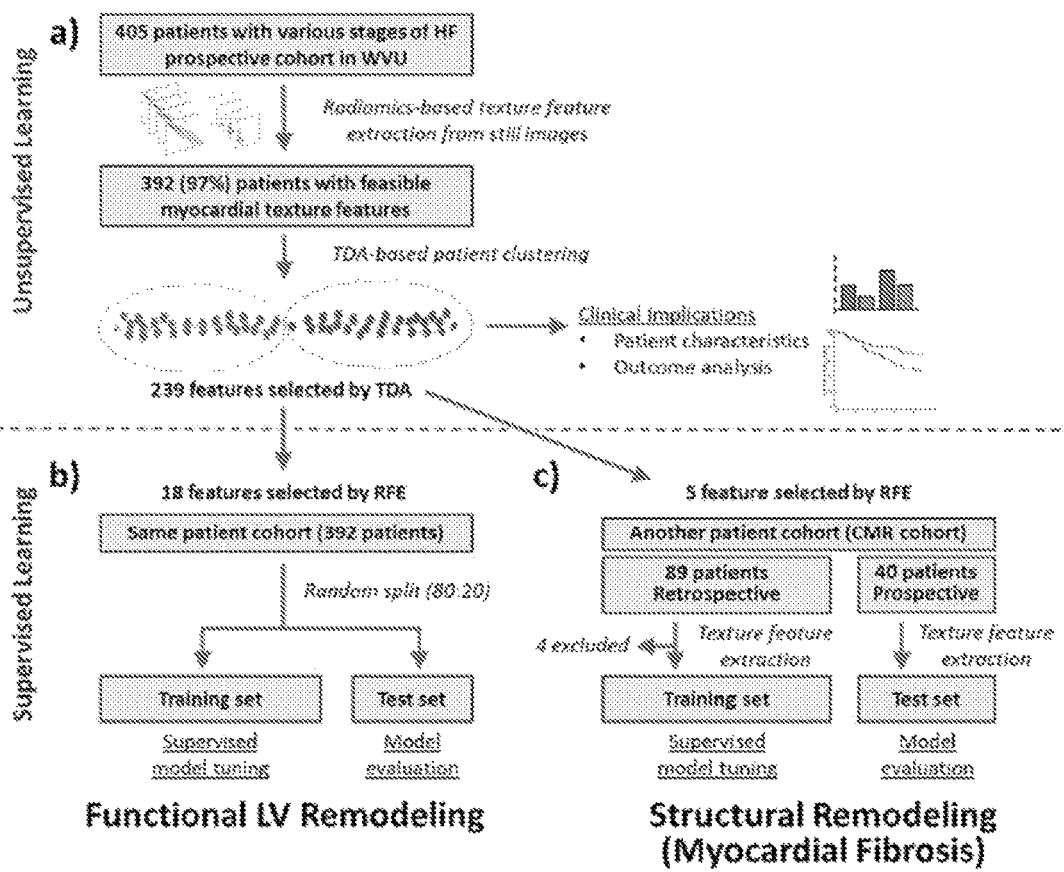
FIG. 10 is an example schematic associated with the process of myocardial fingerprinting according to various embodiments of the present disclosure.

Unsupervised Phenotyping Based on Texture Features (FIG. 10 (*a*))

405 patients were pooled from three prospective studies conducted at West Virginia University between August 2017 and September 2018. Those studies used echocardiography as a reference standard of LV function and were evaluating the value of a surface ECG algorithm to predict diastolic dysfunction (n=196). This study included adult (>18 years old) subjects who underwent ECG and echocardiography on the same day; a probe for estimating pulmonary artery pressure from chest wall (n=145). This study included adults older than 18 years old, admitted to the hospital for HF who had an echocardiogram performed within 48 hours of presentation, and a software for the assessment of intracardiac flow (n=64), which included consecutive adult patients referred for LV function assessment. The common exclusion criteria for all the three studies included patients with inadequate echocardiographic views and patients with chest deformities. Myocardial texture feature extraction was feasible in 392 patients. An unsupervised machine learning using topological data analysis was used for aggregating patients with similar textural properties and compared the patient characteristics, cardiac function, and outcome between the phenogroups.

Supervised Learning-Based Prediction of LV Remodeling (FIG. 10 (b))

The 392 patient cohort as described above was used to develop supervised machine learning models for predicting functional markers of LV remodeling (impairment in LV ejection fraction [LVEF] and global longitudinal strain [GLS]), the cohort was randomly divided into a training (80%) and test (20%) set. Then, machine-learning models were trained in the training set (with cross-validation) and subsequently evaluated in the test set.

Supervised Learning-Based Prediction of Myocardial Fibrosis (FIG. 10 (c))

To assess the value of texture features for predicting the presence of CMR delineated myocardial fibrosis, 89 patients who underwent clinically indicated CMR and cardiac ultrasound within 48 hours between July 2017 and December 2018 were retrospectively identified. Exclusion criteria were patients with inadequate echocardiographic views, patients with chest deformities, and patients who underwent CMR without gadolinium contrast. The retrospective cohort was used to train machine learning models with cross-validation and the developed model was tested in 40 prospective patients who were enrolled with the same inclusion/exclusion criteria.

Data Collection

The New York Heart Association (NYHA) functional class and the heart failure stages defined by the American College of Cardiology and the American Heart Association were used to investigate clinical severity. Major adverse cardiac event (MACE) was predefined as the composite of cardiac death, hospitalization due to myocardial infarction, acute coronary syndrome, heart failure, and arrhythmias and were tracked on an electronic chart and/or telephone interview. The Meta-Analysis Global Group in Chronic (MAGGIC) heart failure risk score was calculated as previously reported. All enrolled patients underwent comprehensive 2-dimensional echocardiography using commercially available ultrasound equipment (Vivid-9/95, GE Healthcare; iE-33, Philips Healthcare; and LISENDO 880, Hitachi Healthcare) with 1-5 MHz phased array probes. Ultrasound images were stored in a DICOM format on the institute's local Picture Archiving and Communication System (PACS). Conventional echocardiographic parameters were analyzed per under the current guidelines. LVEF was measured using 2D disk methods at end-diastole and end-systole. Speckle tracking strain analysis was performed offline using vendor-free software (ImageArena, TomTec Inc.) by observers who were blinded to other information, including the texture-based tissue features. The longitudinal strain was calculated using apical 4-, 2-, and long-axis views, and the averaged value was reported as the GLS. CMR was performed using a 1.5 Tesla scanner (MAGNETOM Arena, Siemens Healthineers, Erlangen, Germany). Late gadolinium enhancement imaging was performed in all subjects in accordance with standard clinical protocols. Late gadolinium enhancement was defined by hyper-enhanced pixels with signal intensities of five standard deviations above the mean of normal myocardium. Patients were considered to have myocardial fibrosis in the studied segments if positive late gadolinium enhancement was seen in any of the anteroseptal and posterior wall myocardial segments (corresponding to the segments where ultrasound ROIs were placed for extracting texture features).

Quantitative Texture-Based Tissue Feature Extraction

Texture-based tissue features of myocardium were extracted from still images of traditional parasternal long axis views using LIFEx software v4.5. This technique of texture-based feature extraction has been popularized in radiology and referred to as 'radiomics'. Using two still frames, an end-diastolic and an end-systolic frame, circular regions of interest (ROIs) including 257 pixels (4-9 millimeter (mm) in diameter) per each, were placed at the basal and mid-segments of the interventricular septum and the left ventricular posterior wall, respectively. The basal and mid-segments were defined as the level of the mitral valve leaflet tips and the papillary muscle. The ROI contents were first resampled in 64 discrete values using the formula:

$R(x)$=round(64*[$I(x)$−min ROI intensity]/[max ROI intensity−min ROI intensity])

Where $R(x)$ is the resampled value of pixel x, $1(x)$ is the intensity of pixel x in the original image, and max and min intensity are the maximum and minimum intensities in the ROI, respectively. The software extracted forty-one texture features, or radiomics features, from each ROI, including first-order statistics such as the maximum, minimum, standard deviation, and the mean value of intensity and histogram features, and second-order indices such as the gray-level co-occurrence matrix (GLCM), gray-level run length matrix (GLRLM), neighboring gray-level dependence matrices (NGLDM), and gray-level zone length matrices (GLZLM).

Feature Phenotyping Using Topological Data Analysis

A total of 328 texture features extracted during diastole and systole were included in the topological data analysis using Ayasdi Workbench v7.4 (Ayasdi Inc., Menlo Park, Calif.). Topological data analysis is a novel mathematical and data analysis approach that establishes the topological and geometrical structure of the data to garner information and patterns from the features in a patient-patient similarity network.

In a topological data analysis-based patient similarity network, patients with similar features (in this study, texture-based tissue features) form a node or a dot, and adjacent nodes, including similar patients, are connected with edges or lines. Accordingly, the relative distance between nodes (more precisely, the minimum number of edges between nodes) represents the similarity of features between the nodes. Thus, clusters or groups of patients with similar features can be identified based on the shape of the network. This notion of linking the shape to meaning using tuning based on Bayesian parameter optimization using an optimization technique called sequential model-based algorithm configuration]. This process was performed with Monte-Carlo cross validation.

Finally, several models with the highest performance were selected and their prediction probabilities were averaged to create an ensemble model (fusion model), which were evaluated in the hold-out (not used in the training process) test set. Such techniques of making fusion models help combining diverse and independent models for reducing the generalization error.

Topical Data Analysis—Technical Details

Topological data analysis (TDA) is a novel data visualization technique and a framework for machine learning that is based on the mathematical concept of topology—a subfield of geometry to study the shape and the topological space. It pertains to the analysis of the space that is invariant under certain transformations in a continuous map of f: X→Y from topological space X to topological space Y. Therefore, there are three fundamental invariants of topology that is pertinent in the properties of the topological space: coordinate invariance, deformative invariance, and compressed representation.

Coordinate invariance of the topological space only concerns the property of the shape rather than the coordination and the arrangement of the object. The orientation of the object possesses no value or information as the shape of the object is topologically same. Similarly, the discernment of the object is consistent in the topological space regardless of its stretching or compression to preserve its deformation invariance. Finally, the compressed representation of the topology concerns with connectivity and continuity of the object to provide the summary and succinct description of the shape.

In TDA, two types of parameters are required to generate the network. First, the finite dataset is used to construct the point cloud in the manifold using similarity measurements by applying one of various metrics such as Euclidean distance, binary Jaccard, Hamming distance, or correlation, to name a few. Second, the function that describes the distribution of the data to create a representative node based on the overlapping bins of the dataset. These vital parameters are referred to as metric and lens, respectively. Unlike metrics, multiple lenses can be applied that are guided by two tuning distinct parameters to balance the network—resolution and gain. While resolution modulates the overlapping bins (or nodes) as identified by clustering, gain controls the overlap between these bins. Nodes that do not contain shared data sample with others depending on the metric and/or resolution and gain, some may remain singleton.

In the present study, numeric data were applied in the generation of the model, thus Norm Correlation (Equation 1 shown below) was selected—a metric that measure numerical data point. The metric normalizes the features selected for generating models to have mean 0 and variance 1 and calculates Pearson's Correlation on the data.

$$\text{Norm}\text{Corr}(X, Y) = 1 - r(X', Y')$$

where X', Y' are the mean-centered and variance-normalized X and Y:

$$r(X, Y) = \frac{N \sum_{i=1}^{N} X_i Y_i - \sum_{i=1}^{N} X_i \sum_{i=1}^{N} Y_i}{\sqrt{N \sum_i X_i^2 - (\sum_i X_i)^2} \sqrt{N \sum_i Y_i^2 - (\sum_i Y_i)^2}}$$

Normalized correlation    Equation 1

Furthermore, TDA utilizes lenses that summarize and separate pertinent information from the noisy data. However, each function that is selected as lenses summarize data diversely. In the present study, multidimensional scaling lenses (both resolution: 30, gain: 3.0, equalized) were applied to the dataset for generating the network. Once the TDA network was generated, the overlaying colors on the network demonstrated typical patients with certain characteristics of the variable chosen such as clinical outcomes in the evaluation of the network Reproducibility of Tissue Texture Top texture-based tissue features for predicting myocardial fibrosis were defined using the top importance gain of the four regions. Variability related to the operator, device settings, and device vendors used were assessed in the study. The interobserver variability of feature extraction was tested in two blinded observers who independently analyzed twenty randomly selected patients and assessed the consistency of the texture features. To test the resistance of the texture features to device settings, changes of texture features were evaluated in different gain settings and image qualities. After adding five levels of gain (to I(x)+20, 1(x)+40, 1(x)+60, 1(x)+80, 1(x)+100) and Gaussian additive noise (mean=0, variance of 0.01, 0.02, 0.03, 0.04, and 0.05) to ten images using MATLAB R2018a (The MathWorks, Natick, Mass., USA), the texture features were extracted using exactly the same ROIs. Lastly, the vendor dependency of the texture features were verified by testing topological data analysis-based patient similarity networks generated using features extracted from two vendors (GE Healthcare and Hitachi Healthcare).

Statistical Analysis

Data are presented as the median [1st and 3rd interquartile range] for continuous variables and as the frequency (%) for categorical variables. Group differences were evaluated using Mann-Whitney U tests for continuous variables and chi-square or Fisher's exact tests for categorical variables. Kaplan-Meier curve analysis, the log-rank test, and multivariable Cox proportional hazard models were used for survival analysis. The ROC curves of the machine learning models were drawn, and the best thresholds were identified based on the Youden index. Interobserver variability was evaluated using Pearson's r and interclass correlation coefficients. All statistical analyses were performed with R version 3.5.2 (The R Foundation for Statistical Computing, Vienna, Austria). A two-tailed p<0.05 indicated statistical significance.

Results

Unsupervised Phenotyping Based on Texture Features

For the first part of the study (FIG. 10 (a)), 328 texture features were successfully extracted from still-frame ultrasound images in 392 of the 405 (97%) subjects. Overall, the median age of the population was 58 [45_68] years, 55.9% were female, 26.3% had severe heart failure symptoms (NYHA class III or IV) and 32.9% had stage C or D heart failure. Using the extracted texture features, unsupervised topological data analysis identified a bar-shaped patient similarity network, where two clusters were connected by a single node (FIG. 11(a)). Clusters A and B included 196 and 210 patients, respectively, with fourteen (14) patients overlapping between the groups. Interestingly, these identified clusters had significantly different clinical and echocardiographic characteristics even though the clusters were created using only the texture features of still images. Group differences are summarized in Table 1.

tion from still routine ultrasound images and classified patients in a clinically meaningful way.

Comparison of Clinical Outcomes Between Clusters

Figure 12A:
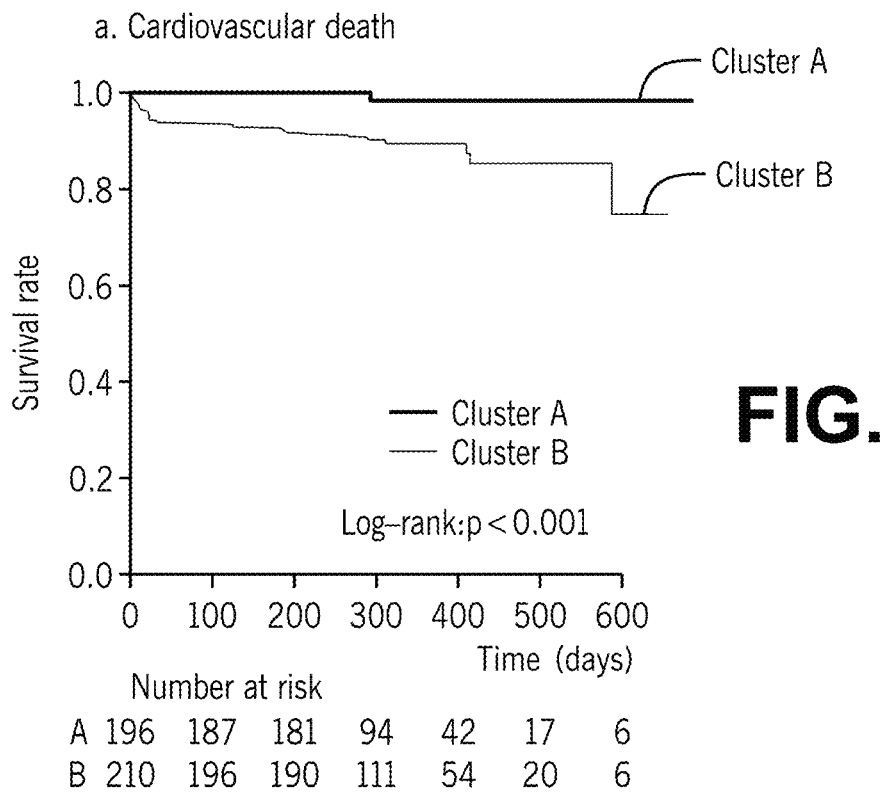
FIGS. 12A-12B are example graphical representations illustrating clinical outcomes between clusters according to various embodiments of the present disclosure.
Figure 12B:
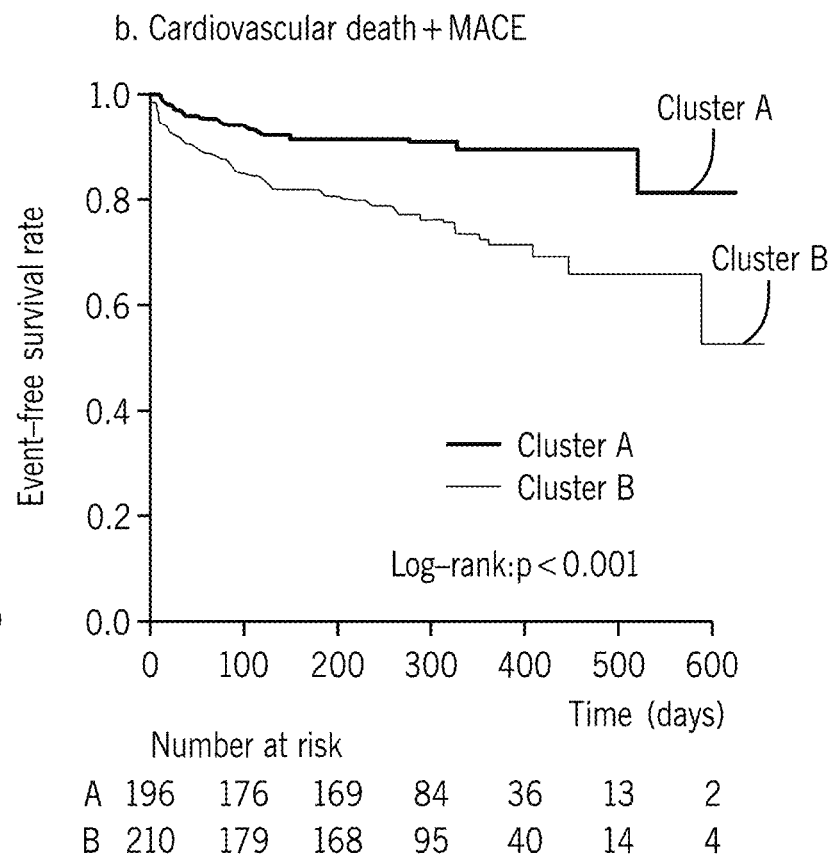

The clinical prognosis of the two clusters were also compared. During the follow-up period of a median of 301 [268-323] days, 76 MACEs, including 26 cardiac deaths, were observed. Kaplan-Meier curves showed that patients in cluster B had a significantly higher incidence of cardiac death and MACE than those in cluster A (p<0.001 by log-rank test, for both, FIGS. 12A-12B). Cox proportional hazard models showed that even after adjusting for the

TABLE 1

Patient characteristics.

| Factor | Overall | Cluster A | Cluster B | p value |
|---|---|---|---|---|
| Number of patients | 392 | 196 | 210 | |
| Age, years | 58 [45-68] | 54 [40-65] | 61 [50-71] | <0.001 |
| Female, n (%) | 219 (55.9) | 113 (57.7) | 113 (53.8) | 0.484 |
| BSA, m$^2$ | 2.02 [1.8-2.22] | 2.03 [1.84-2.23] | 1.97 [1.77-2.20] | 0.041 |
| BMI, kg/m$^2$ | 29.2 [25.7-36.0] | 29.9 [25.7-37.4] | 28.8 [25.7-33.8] | 0.113 |
| Coronary artery disease, n (%) | 148 (37.8) | 63 (32.1) | 90 (42.9) | 0.031 |
| Hypertension, n (%) | 272 (69.4) | 133 (67.9) | 148 (70.5) | 0.592 |
| Cerebral vessel disease, n (%) | 46 (11.8) | 21 (10.7) | 25 (12.0) | 0.755 |
| Diabetes mellitus, n (%) | 119 (30.4) | 50 (25.5) | 72 (34.3) | 0.065 |
| Atrial fibrillation, n (%) | 50 (12.8) | 12 (6.1) | 42 (20.0) | <0.001 |
| NYHA ≥ III, n (%) | 103 (26.3) | 37 (18.9) | 73 (34.8) | <0.001 |
| HF stages C or D, n (%) | 129 (32.9) | 56 (28.6) | 78 (37.1) | 0.073 |
| Echocardiography | | | | |
| IVSd, mm | 10 [9-12] | 10 [8-12] | 11 [9-13] | 0.005 |
| PWd, mm | 9 [8-11] | 9 [8-10] | 9 [8-11] | 0.068 |
| LVIDd, mm | 46 [42-51] | 46 [42-49] | 47 [42-52] | 0.036 |
| LVIDs, mm | 32 [28-37] | 31 [28-35] | 34 [29-40] | <0.001 |
| LVEDVi, mL/m$^2$ | 52 [43-64] | 50 [41-60] | 56 [45-68] | <0.001 |
| LVESVi, mL/m$^2$ | 21 [15-28] | 19 [15-26] | 22 [16-33] | <0.001 |
| LA volume index, mL/m$^2$ | 25 [20-35] | 23 [18-32] | 28 [21-41] | <0.001 |
| LV mass index, mg/m2 | 76 [59-101] | 72 [56-90] | 82 [64-112] | <0.001 |
| E wave velocity, m/s | 0.84 [0.69-0.96] | 0.81 [0.69-0.94] | 0.87 [0.70-1.01] | 0.057 |
| A wave velocity, m/s | 0.70 [0.54-0.89] | 0.70 [0.53-0.89] | 0.70 [0.55-0.90] | 0.897 |
| E/A ratio | 1.14 [0.85-1.55] | 1.11 [0.85-1.51] | 1.16 [0.84-1.56] | 0.720 |
| e', cm/s | 8.1 [6.0-10.5] | 8.5 [7.0-10.7] | 7.6 [5.5-10.5] | 0.001 |
| E/e' | 9.3 [7.2-14.5] | 9.0 [7.2-12] | 10.1 [7.7-17.2] | 0.003 |
| LVEF, % | 60 [53-65] | 61 [55-65] | 59 [46-65] | 0.011 |
| GLS, absolute % | 19.3 [15.7-22.0] | 20.2 [18.1-23.5] | 17.3 [12.5-20.4] | <0.001 |
| LV hypertrophy, n (%) | 84 (21.4) | 23 (11.7) | 63 (30.0) | <0.001 |
| LV diastolic function, n (%) | | | | <0.001 |
| normal | 188 (49.3) | 120 (61.9) | 74 (36.8) | |
| grade 1 | 29 (7.6) | 10 (5.2) | 20 (10.0) | |
| grade 2 | 63 (16.5) | 22 (11.3) | 45 (22.4) | |
| grade 3 | 34 (8.9) | 8 (4.1) | 27 (13.4) | |
| indeterminate | 61 (16.0) | 31 (16.0) | 32 (15.9) | |
| indeterminate grade | 6 (1.6) | 3 (1.5) | 3 (1.5) | |

Figure 11:
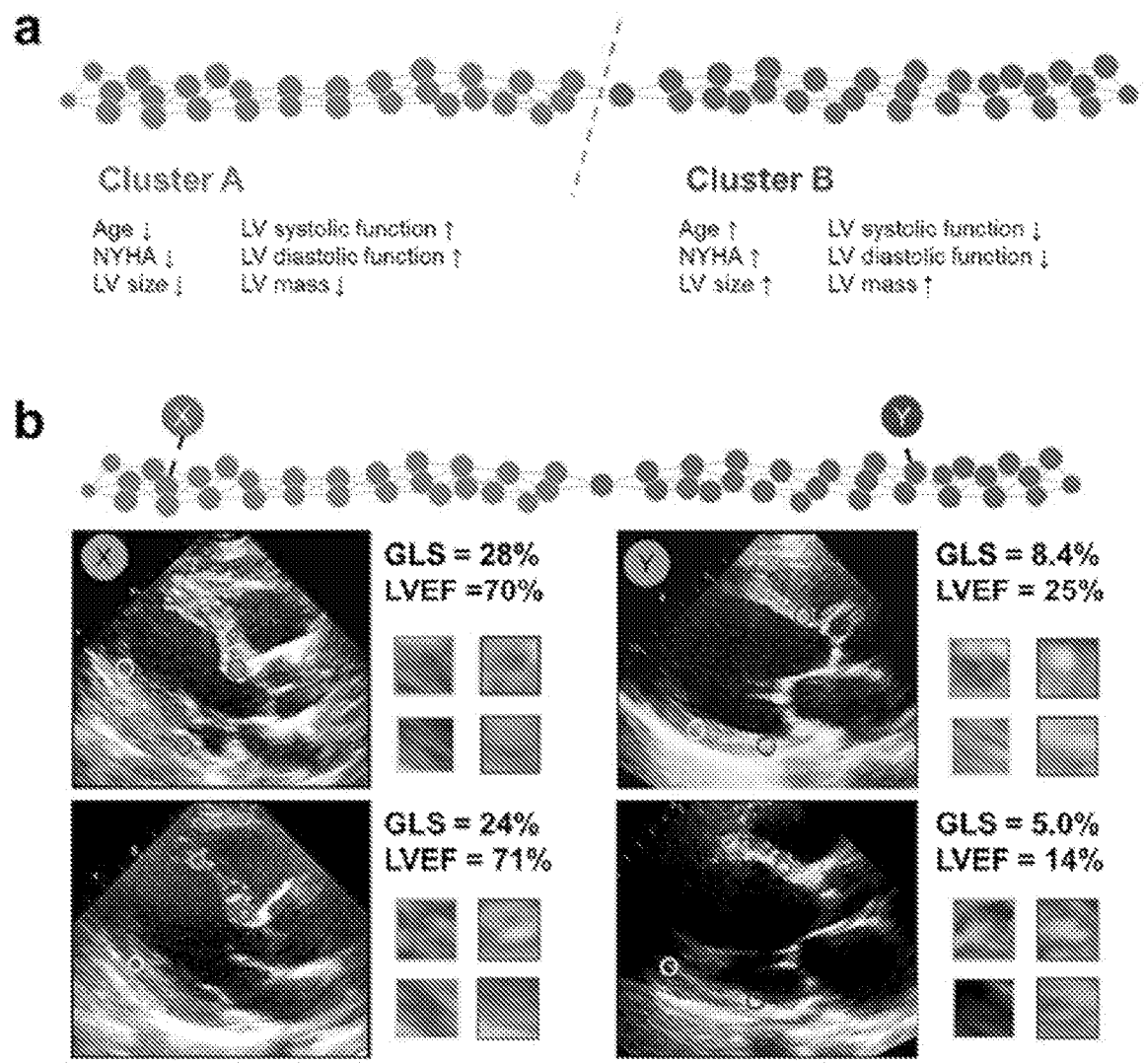
FIG. 11 is an example drawing illustrated patient similarity based on myocardial texture features according to various embodiments of the present disclosure.

Compared with cluster A, cluster B was associated with greater age and more advanced heart failure. Furthermore, patients in cluster B had significant differences in LV remodeling: the intraventricular septum and LV mass index were greater, the LV dimensions and volumes were larger, the LVEF and LV GLS were reduced, the LV diastolic function represented by tissue Doppler e' and E/e' was impaired, and the left atrial volume was larger compared to those in cluster A (Table 1). Illustrative cases for each cluster are shown in FIG. 11(b). Although functional evaluation of the myocardial textures in the images seems unfeasible with the human eye, this texture-based approach was able to identify important information for evaluating cardiac func- MAGGIC score, a well-established risk score for patients with heart failure validated in various clinical settings, texture-based clustering was significantly associated with cardiac death (HR 6.23, 95% CI 1.46-26.5, p=0.013 by Cox proportional hazard analysis). The association of texture-based clustering with MACE was significant in the univariate model (HR 2.85, 95% CI 1.69-4.78, p<0.001 by Cox proportional hazard analysis) and a model adjusted with other clinical factors (age, sex, body mass index, history of coronary heart disease, hypertension, and LVEF; HR 1.74, 95% CI 1.01-3.00, p=0.047 by Cox proportional hazard analysis), and showed borderline significance in a model adjusted with the MAGGIC score (HR 1.68, 95% CI 0.99-2.87, p=0.057 by Cox proportional hazard analysis). The results for the Cox models are summarized in Table 2.

TABLE 2

Cox regression models.

| | For cardiac death | | | For MACE | | |
|---|---|---|---|---|---|---|
| | HR | 95% CI | p value | HR | 95% CI | p value |
| Cluster B | 11.09 | 2.62-46.93 | 0.001 | 2.85 | 1.69-4.78 | <0.001 |
| Adjustment for MAGGIC score | 6.23 | 1.46-26.50 | 0.013 | 1.68 | 0.99-2.87 | 0.057 |
| Adjustment for clinical factors* | | | | 1.74 | 1.01-3.00 | 0.047 |

Supervised Learning-Based Prediction of Functional LV Remodeling

Figure 13A:
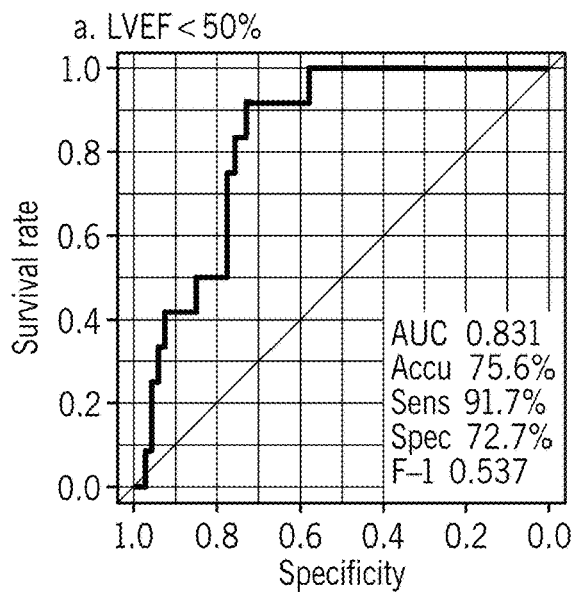
FIGS. 13A-13C are example graphical representations illustrating the direct prediction of impaired cardiac function according to various embodiments of the present disclosure.
Figure 13B:
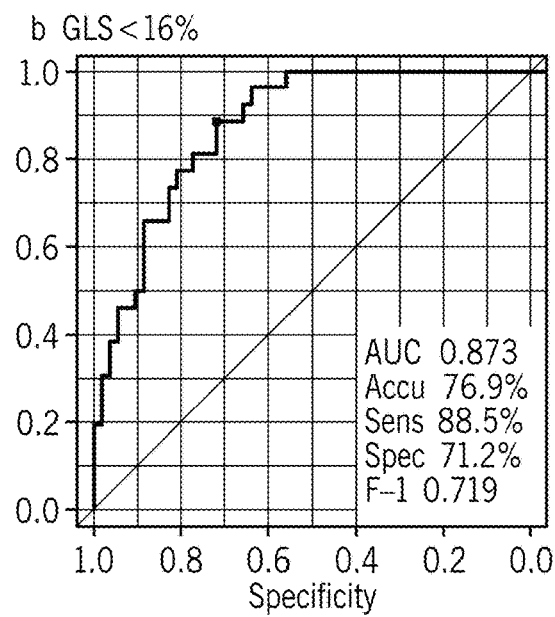
Figure 13C:
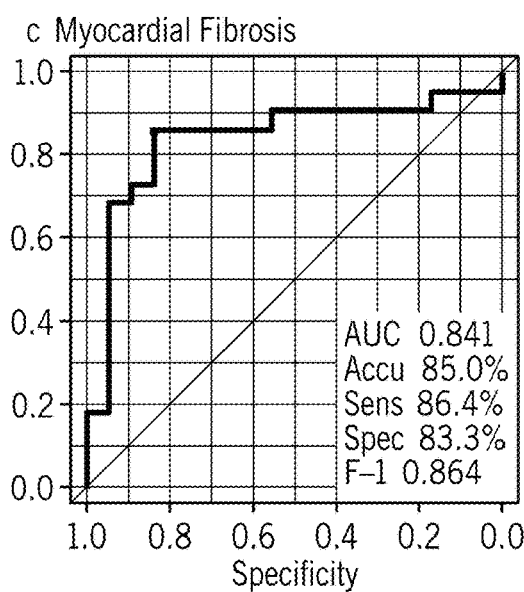

This part is summarized in the bottom left of FIG. 10. To explore the value of the texture-based tissue features to directly predict functional LV remodeling, the patient cohort was randomly divided into training (80%) and test set (20%), and supervised machine learning algorithms were trained in the training set using only the texture features extracted from the still images. Topological data analysis and subsequent recursive feature elimination were used for feature selection and 18 features per each were used to train prediction models for reduced LVEF (<50%) and GLS (<16%). Panel A and B in FIGS. 13A-13C show the ROC curves for the prediction of reduced LVEF and GLS obtained in the test set. The best model for predicting reduced LVEF was an ensemble of 10 models (2 boosted trees, 3 random decision forests, 2 LASSO regressions, 2 ridge regressions, and 1 neural network) and showed performance of ROC AUC 0.83, sensitivity 91.7%, and specificity 72.3%, whereas the one for impaired GLS was an ensemble of 10 different models (5 bootstrap decision forest, 2 ridge regressions, 2 LASSO regressions, and 1 neural network) and had ROC AUC of 0.87, sensitivity of 88.5%, and specificity of 71.2%.

Supervised Learning-Based Prediction of Myocardial Fibrosis

For investigating the value of the cardiac ultrasound texture-based features in predicting whether the patient has myocardial fibrosis detected by CMR, 89 retrospectively identified patients who had undergone CMR and echocardiography within 48 hours were studied as the training set, and 40 independent prospective patients were studied as the test set, as shown in FIG. 10 (b). Texture feature extraction was feasible in 85 (96%) and 40 (100%) patients, respectively. The clinical characteristics of the training and test set are summarized in Table 3.

TABLE 3

Patient characteristics of the patients with a magnetic resonance scan.

| Factor | Retrospective (training) | Prospective (rest) | p value |
|---|---|---|---|
| Number of patients | 85 | 40 | |
| Age, years | 55 [41-66] | 56 [46-64] | 0.667 |
| Female, n (%) | 53 (62.4) | 16 (40.0) | 0.022 |
| BSA, m$^2$ | 2.03 (0.35) | 2.03 (0.27) | 0.984 |
| BMI, kg/m$^2$ | 55.37 (231.98) | 29.77 (6.23) | 0.488 |
| Coronary artery disease, n (%) | 38 (44.7) | 13 (33.3) | 0.246 |
| Hypertension, n (%) | 43 (50.6) | 27 (69.2) | 0.078 |
| Cerebral vessel disease, n (%) | 6 (7.1) | 3 (12.5) | 0.410 |
| Diabetes mellitus, n (%) | 21 (24.7) | 13 (33.3) | 0.387 |
| Atrial fibrillation, n (%) | 8 (9.4) | 4 (10.3) | >0.99 |
| NYHA ≥ III, n (%) | 12 (14.1) | 16 (40.0) | 0.002 |
| HF stages C or D, n (%) | 17 (20.0) | 21 (52.5) | <0.001 |
| Echocardiography | | | |
| IVSd, mm | 10 [8-12] | 10 [9-11] | 0.983 |
| PWd, mm | 9 [8-11] | 10 [9-11] | 0.503 |
| LVIDd, mm | 48 [42-53] | 46 [45-57] | 0.163 |
| LVIDs, mm | 34 [29-42] | 35 [30-48] | 0.378 |
| LVEDVi, mL/m$^2$ | 54 [40-67] | 57 [45-69] | 0.537 |
| LVESVi, mL/m$^2$ | 23 [16-40] | 27 [20-45] | 0.168 |
| LA volume index, mL/m$^3$ | 22 [18-33] | 32 [21-39] | 0.011 |
| LV mass index, mg/m2 | 79 [67-103] | 96 [70-132] | 0.057 |
| E wave velocity, m/s | 0.85 [0.62-1.00] | 0.86 [0.69-1.00] | 0.816 |
| A wave velocity, m/s | 0.60 [0.51-0.84] | 0.68 [0.49-0.83] | 0.980 |
| E/A ratio | 1.26 [0.84-1.77] | 1.16 [0.90-1.66] | 0.810 |
| e', cm/s | 9 [6-12] | 8 [6-11] | 0.317 |
| E/e' | 8.4 [6.6-11.3] | 10.4 [7.6-14.8] | 0.093 |
| LVEF, % | 55 [42-63] | 48 [34-56] | 0.023 |
| GLS, absolute % | NA | 12.8 [7.9-19.4] | NA |
| LV hypertrophy, n (%) | | | 0.136 |
| LV diastolic function, n (%) | | | 0.173 |
| Normal | 17 (20.0) | 3 (8.3) | |
| Grade 1 | 28 (32.9) | 11 (30.6) | |
| Grade 2 | 18 (21.2) | 15 (41.7) | |
| Grade 3 | 17 (20.0) | 5 (13.9) | |
| Indeterminate | 5 (5.9) | 2 (5.6) | |
| Indeterminate grade | 0 (0.0) | 0 (0.0) | |

There were 48 (56.4%) and 22 (55.0%) patients who had myocardial fibrosis in at least one of the four ROIs where the texture features were extracted using the ultrasound images in the training and test set, respectively.

Out of the extracted texture features, feature selection was performed and five best features were identified to develop supervised machine learning models. The models were trained to predict whether the patient has myocardial fibrosis using cross-validation in the training set (FIGS. 5A-5C). In the test set, the developed model (an ensemble of 2 LASSO regressions) predicted myocardial fibrosis with an ROC AUC of 0.84 (sensitivity 86.4%, and specificity 83.3%).

Robustness of Texture-Based Feature Extraction

To confirm the stability of the texture features, the variability related to the operator, image quality, and device vendors used in the study were accessed. Briefly, most features had a good interobserver agreement with interclass correlation coefficient 0.74-0.96, except for correlation in GLCM (0.54). The noise and gain on each image were artificially increased and the change of the features was tested. As shown, each feature showed different behavior against increases in gain and noise. For example, gray-level non-uniformity of the GLRLM, the second most important feature for predicting functional LV remodeling, was resistant to an increase in gain, while it markedly increased with additional noise in the images. On the other hand, the high gray-level run emphasis of GLCM, one of the important features for predicting myocardial fibrosis, was relatively resistant to an increase in noise, whereas it dramatically increased with additional gains on the images. To elucidate the value of the texture features among different vendors, patient similarity networks were created using data obtained from each of the two dominant vendors using topological data analysis. The created networks from both vendors formed similar loops, where most patients with reduced LV systolic function were segregated in a part of a loop, suggesting that the information content of the texture features were relatively invariant to the data source.

Discussion

In the present study, the texture-based analysis was illustrated to be feasible for most clinical cardiac ultrasound (97%), unsupervised patient-similarity analysis revealed that a specific pattern of information from myocardial texture was associated with functional LV remodeling, advanced heart failure, and adverse clinical outcome, and the texture features extracted from still cardiac ultrasound images could be used for developing supervised machine learning models that enable clinical prediction of functional and structural LV remodeling. Texture-based analysis has been recently used in radiology (also referred to as radiomics) to extract maximal information from standard-of-care images using high-throughput computing. The present disclosure resembles the general principles of radiomics and specifically defines a computational pipeline where texture-based tissue features were extracted and used for building supervised machine learning models for individualized predictions. This approach may potentially address a long-described objective of cardiac ultrasound in providing myocardial tissue characterization in clinical practice.

It is well known that in typical cases, the pathological myocardial texture is visually distinguishable with ultrasound images. For example, scar lesions after myocardial infarction have high echo intensity and thin walls, and myocardium with infiltration of amyloid has a granular sparkling texture. However, many previous attempts to characterize myocardial tissue using ultrasound images, such as integrated backscatter analysis, have resulted in suboptimal results because of variations in the quality and texture of the cardiac ultrasound images. As a consequence, in current clinical practice, CMR imaging is preferred modality for myocardial tissue characterization using late gadolinium enhancement imaging and methods such as parametric and non-parametric T1, T2 and T2* imaging. However, due to its cost, accessibility, and contraindications, CMR is not available for every patient and in every place. Since cardiac ultrasound remains portable, low-cost, and the most common cardiac imaging procedure performed in clinical practice, implementation of tissue characterization with cardiac ultrasound may have a wider clinical impact. In the initial attempt, the use of cardiac ultrasound texture-based tissue features of myocardium were illustrated to be robust and concordant in several steps of analyses: i.e., cluster analysis with topological data analysis with clinical outcome prediction; supervised machine learning analysis for predicting impaired LV systolic function; and identification of the presence of myocardial fibrosis.

The segregation of high-risk myocardium was also show to be vendor-independent and that interobserver agreement was adequate for clinical application. These results reconfirmed that important information associated with myocardial remodeling that can be captured by CMR is also carried in ultrasound texture features and can be retrieved using a modern high-throughput computing pipeline, which possibly amended the signal to noise ratio and helped extraction of useful information from noisy ultrasound data.

Although some features were sensitive to changes in gain or noise, the majority of the features were stable and resistant to the changes in image quality. Although radiomics-based texture analysis approach in this study, deep learning may be another choice of approaches with which images can be analyzed in an end-to-end pipeline. Both deep learning and radiomics have received considerable attention in recent years in radiology and the relative merits of both techniques remains an area of active investigation. While some investigators have only recently compared the two approaches citing the advantage of deep learning approaches for radiological images, others have suggested that both approaches are complementary and can unite in the future to produce a single unified framework. Such comparative studies have been performed mostly in radiology, in general, and the application of radiomics for cardiac imaging is still in its infancy.

The embodiments of the present disclosure are novel with respect to the application of traditional radiomics approach to extract semantic and agnostic features from cardiac ultrasound images for predicting LV remodeling. A recent successful application of handcrafted radiomics features in myocardial tissue characterization further supports the choice of restricting the initial analysis to only using handcrafted radiomics approach. While deep learning based radiomics may have several advantages including its generalization capability and its independence from the supervision of experts, the lack of reproducibility and interpretability, as well as over-fitting on small datasets like those of the present disclosure, pose substantial challenges in readily adapting deep networks for this study.

In addition to the foregoing, the various embodiments of the present disclosure include, but are not limited to, the embodiments set for in the following clauses.

Clause 1. A system, comprising: at least one computing device; and at least one application executable on the at least one computing device, wherein, when executed, the at least one application causes the at least one computing device to at least: extract a plurality of radiomic features from an ultrasound image associated with a patient; determine one or more myocardial characteristics by applying the extracted plurality of radiomic features to one or more phenotyping models; and interpret a clinical significance associated with the patient based at least in part on the one or more myocardial characteristics and the extracted plurality of radiomic features.

Clause 2. The system of clause 1, wherein the ultrasound image comprises a plurality of ultrasound images.

Clause 3. The system of clause 1, wherein the ultrasound image is a static image.

Clause 4. The system of any one of clauses 1-3, wherein, when executed, the at least one application causes the at least one computing device to at least identify a selection of a region of interest in the ultrasound image, the plurality of radiomics features being extracted within the region of interest.

Clause 5. The system of any one of clauses 1-4, wherein the radiomic features are extracted from a pixel-based pattern in the ultrasound image.

Clause 6. The system of any one of clauses 1-5, wherein, when executed, the at least one application further causes the at least one computing device to at least identify one or more myocardial textures based at in part on a clustering of the extracted plurality of radiomic features.

Clause 7. The system of any one of clauses 1-6, wherein the ultrasound image is of a region of a heart.

Clause 8. The system of any one of clauses 1-7, wherein the clinical significance is further based at least in part on matching the plurality of radiomic features to a patient cluster.

Clause 9. The system of any one of clauses 1-8, wherein the clinical significance is further based at least in part on matching the radiomic features to a gradient of a patient cluster.

Clause 10. The system of any one of clauses 1-9, wherein the clinical significance comprises at least one of a ventricular malformation, a risk of advanced heart failure, myocardial fibrosis, one or more cardiac malignancies, or heart valve deterioration.

Clause 11. The system of any one of clauses 1-10, wherein the one or more phenotyping models comprise at least one of a neural network classifier, a support vector machine (SVM) classifier, or a deep learning classifier.

Clause 12. The system of any one of clauses 1-11, wherein, when executed, the at least one application further causes the at least one computing device to at least: select a portion of the plurality of radiomics features; select at least one of the one or more phenotyping models based at least in part on the portion of the plurality of radiomics features; and determine the one or more myocardial characteristics is based at least in part on the portion of the plurality of radiomics features and the at least one of the one or more phenotyping models.

Clause 13. A method, comprising: extracting, via at least one computing device, a plurality of radiomic features from an ultrasound image associated with a person; identifying, via the at least one computing device, one or more myocardial textures by applying the extracted plurality of radiomic features to at least one phenotyping model; and determining, via the at least one computing device, at least one condition associated with the person based at least in part on the one or more myocardial textures and the extracted plurality of radiomic features.

Clause 14. The method of clause 13, further comprising: comparing, via the at least one computing device, the one or more myocardial textures to at least one phenotype cluster for at least one known condition; a determining the at least one condition is based at least in part on the one or more myocardial textures being matched with one or more of the at least one phenotype cluster.

Clause 15. The method of any one of clauses 13-14, further comprising obtaining, via at least one computing device, the ultrasound image from an ultrasound capturing device in data communication with the at least one computing device.

Clause 16. The method of any one of clauses 13-15, wherein extracting the plurality of radiomic features from the ultrasound image further comprises detecting pixel-based patterns in the ultrasound image.

Clause 17. The method of any one of clauses 13-16, further comprising identifying, via the at least one computing device, at least one selected region of interest in the ultrasound image, wherein the plurality of radiomic features are extracted from the at least one selected region of interest in the ultrasound image.

Clause 18. The method of any one of clauses 13-17, wherein the at least one condition comprises at least one of a ventricular malformation, a risk of advanced heart failure, myocardial fibrosis, one or more cardiac malignancies, or heart valve deterioration.

Clause 19. The method of any one of clauses 13-18, wherein the one or more phenotyping models comprise at least one of a neural network classifier, a support vector machine (SVM) classifier, or a deep learning classifier.

Clause 20. The method of any one of clauses 13-19, wherein the ultrasound image comprises a static two-dimensional cardiac ultrasound image.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A system, comprising:
   at least one computing device; and
   at least one application executable on the at least one computing device, wherein, when executed, the at least one application causes the at least one computing device to at least:
   extract a plurality of radiomic features from an ultrasound image associated with a patient;
   determine one or more myocardial characteristics by applying the extracted plurality of radiomic features to one or more phenotyping models; and
   interpret a clinical significance associated with the patient based at least in part on the one or more myocardial characteristics and matching the extracted plurality of radiomic features to a patient cluster mapping.

2. The system of claim 1, wherein the ultrasound image comprises a plurality of ultrasound images.

3. The system of claim 1, wherein the ultrasound image is a static image.

4. The system of claim 1, wherein, when executed, the at least one application causes the at least one computing device to at least identify a selection of a region of interest in the ultrasound image, the plurality of radiomics features being extracted within the region of interest.

5. The system of claim 1, wherein the radiomic features are extracted from a pixel-based pattern in the ultrasound image.

6. The system of claim 1, wherein, when executed, the at least one application further causes the at least one computing device to at least identify one or more myocardial textures based at least in part on a clustering of the extracted plurality of radiomic features.

7. The system of claim 1, wherein the ultrasound image is of a region of a heart.

8. The system of claim 1, wherein the clinical significance is further based at least in part on matching the radiomic features to a gradient of a patient cluster.

9. The system of claim 1, wherein the clinical significance comprises at least one of a ventricular malformation, a risk of advanced heart failure, myocardial fibrosis, one or more cardiac malignancies, or heart valve deterioration.

10. The system of claim 1, wherein the one or more phenotyping models comprise at least one of a neural network classifier, a support vector machine (SVM) classifier, or a deep learning classifier.

11. The system of claim 1, wherein, when executed, the at least one application further causes the at least one computing device to at least:
   select a portion of the plurality of radiomics features;
   select at least one of the one or more phenotyping models based at least in part on the portion of the plurality of radiomics features; and
   determine the one or more myocardial characteristics is based at least in part on the portion of the plurality of radiomics features and the at least one of the one or more phenotyping models.

12. A method, comprising:
   extracting, via at least one computing device, a plurality of radiomic features from an ultrasound image associated with a person;
   identifying, via the at least one computing device, one or more myocardial textures by applying the extracted plurality of radiomic features to at least one phenotyping model;
   comparing, via the at least one computing device, the one or more myocardial textures to at least one phenotype cluster mapping for at least one known condition; and
   determining, via the at least one computing device, at least one condition associated with the person based at least in part on the one or more myocardial textures being matched with one or more of the at least one phenotype cluster mapping, and the extracted plurality of radiomic features.

13. The method of claim 12, further comprising obtaining, via at least one computing device, the ultrasound image from an ultrasound capturing device in data communication with the at least one computing device.

14. The method of claim 12, wherein extracting the plurality of radiomic features from the ultrasound image further comprises detecting pixel-based patterns in the ultrasound image.

15. The method of claim 12, further comprising identifying, via the at least one computing device, at least one selected region of interest in the ultrasound image, wherein the plurality of radiomic features are extracted from the at least one selected region of interest in the ultrasound image.

16. The method of claim 12, wherein the at least one condition comprises at least one of a ventricular malformation, a risk of advanced heart failure, myocardial fibrosis, one or more cardiac malignancies, or heart valve deterioration.

17. The method of claim 12, wherein the one or more phenotyping models comprise at least one of a neural network classifier, a support vector machine (SVM) classifier, or a deep learning classifier.

18. The method of claim 12, wherein the ultrasound image comprises a static two-dimensional cardiac ultrasound image.

* * * * *